(12) United States Patent
Abbaspourrad et al.

(10) Patent No.: US 12,064,766 B2
(45) Date of Patent: *Aug. 20, 2024

(54) RHEOTAXIS-BASED SEPARATION OF MOTILE SPERM AND BACTERIA USING A MICROFLUIDIC CORRAL SYSTEM

(71) Applicant: Cornell University, Ithaca, NY (US)

(72) Inventors: Alireza Abbaspourrad, Ithaca, NY (US); Meisam Zaferani, Ithaca, NY (US); Soon Hon Cheong, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/981,711

(22) Filed: Nov. 7, 2022

(65) Prior Publication Data
US 2023/0311124 A1  Oct. 5, 2023

Related U.S. Application Data

(63) Continuation of application No. 16/374,529, filed on Apr. 3, 2019, now Pat. No. 11,491,485.
(Continued)

(51) Int. Cl.
*B01L 3/00* (2006.01)
*C12N 1/20* (2006.01)
(Continued)

(52) U.S. Cl.
CPC ... *B01L 3/502753* (2013.01); *B01L 3/502707* (2013.01); *C12N 1/20* (2013.01);
(Continued)

(58) Field of Classification Search
CPC ....... B01L 2300/087; B01L 2300/0877; B01L 2300/089; B01L 2200/0652;
(Continued)

(56) References Cited

U.S. PATENT DOCUMENTS 9,663,755 B2    5/2017  Nosrati et al.
11,708,556 B2 *  7/2023  Gale .................. C12M 47/04
                                                 435/325
(Continued)

FOREIGN PATENT DOCUMENTS

WO   WO-2017127775 A1 *  7/2017  ........ B01L 3/502746

OTHER PUBLICATIONS

Marcos et al., "Bacterial Rheotaxis," PNAS., 109(13): 4780-4785 (2012).
(Continued)

*Primary Examiner* — Jennifer Wecker
*Assistant Examiner* — Kathryn Elizabeth Limbaugh
(74) *Attorney, Agent, or Firm* — Troutman Pepper Hamilton Sanders LLP (Rochester)

(57) ABSTRACT

The present application relates to a microfluidic system and its method for use for the separation of motile sperm from immotile sperm or motile bacteria from immotile bacteria. The system includes a housing having a first end, and a second end, with a passage connecting the first and second ends. There is an inlet at the first end of the housing for charging fluids into the passage and an outlet at the second end of said housing for discharging fluids from the passage. There are one or more corrals within the passage, each of the corrals including a closed side and a partially open side. The closed side of the corrals is closer to the first end than the partially open side, with the closed side and partially open side defining between them a confinement region suitable for retaining motile sperm or motile bacteria.

22 Claims, 19 Drawing Sheets

Related U.S. Application Data

(60) Provisional application No. 62/654,976, filed on Apr. 9, 2018.

(51) Int. Cl.
*C12N 5/071* (2010.01)
*C12N 5/076* (2010.01)

(52) U.S. Cl.
CPC ............ *C12N 5/061* (2013.01); *C12N 5/0612* (2013.01); *B01L 2200/0652* (2013.01); *B01L 2300/087* (2013.01); *B01L 2300/0877* (2013.01); *B01L 2300/089* (2013.01)

(58) Field of Classification Search
CPC ......... B01L 3/502753; B01L 3/502707; C12N 1/20; C12N 5/061; C12N 5/0612
See application file for complete search history.

(56) References Cited

U.S. PATENT DOCUMENTS

| | | |
|---|---|---|
| 2014/0248656 A1 | 9/2014 | Demirci et al. |
| 2015/0140655 A1* | 5/2015 | Nosrati .................. C12M 47/04 |
| | | 435/366 |
| 2016/0017273 A1 | 1/2016 | Yamashita et al. |
| 2017/0182288 A1 | 6/2017 | Stone et al. |
| 2018/0282676 A1 | 10/2018 | Vollmer |
| 2019/0308192 A1 | 10/2019 | Abbaspourrad et al. |
| 2021/0178394 A1* | 6/2021 | Asghar .................. A61D 19/02 |

OTHER PUBLICATIONS

Kantsler et al., "Rheotaxis Facilitates Upstream Navigation of Mammalian Sperm Cells," eLife, 3:e02403 (2014).

* cited by examiner

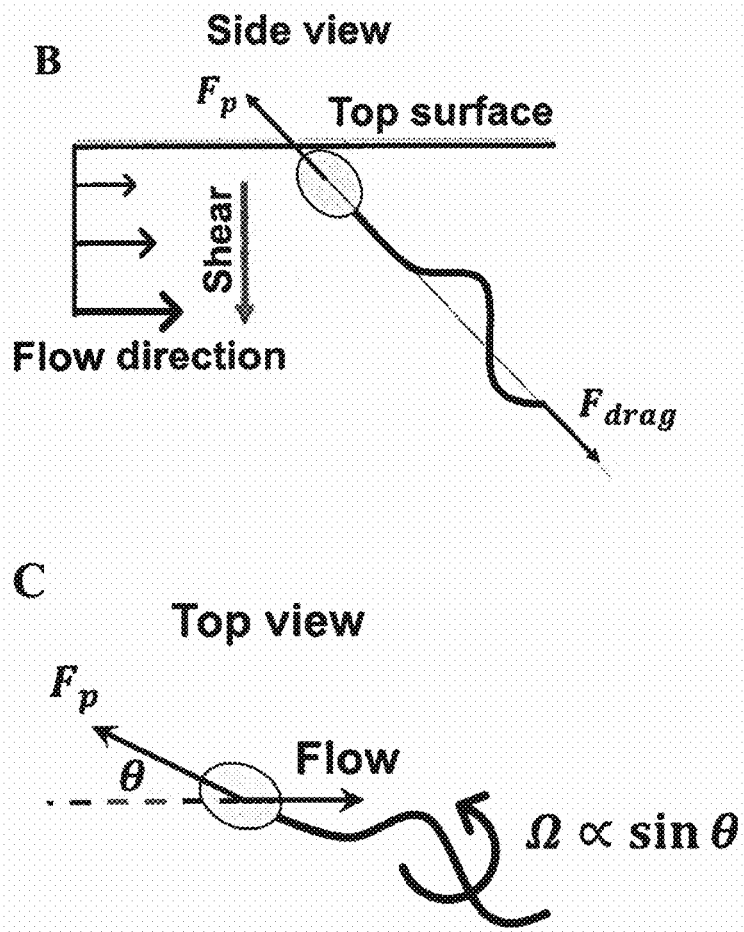
FIGs. 1B-C
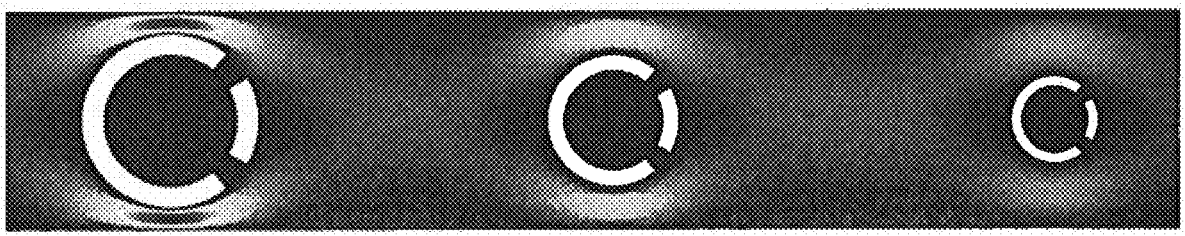
FIG. 2

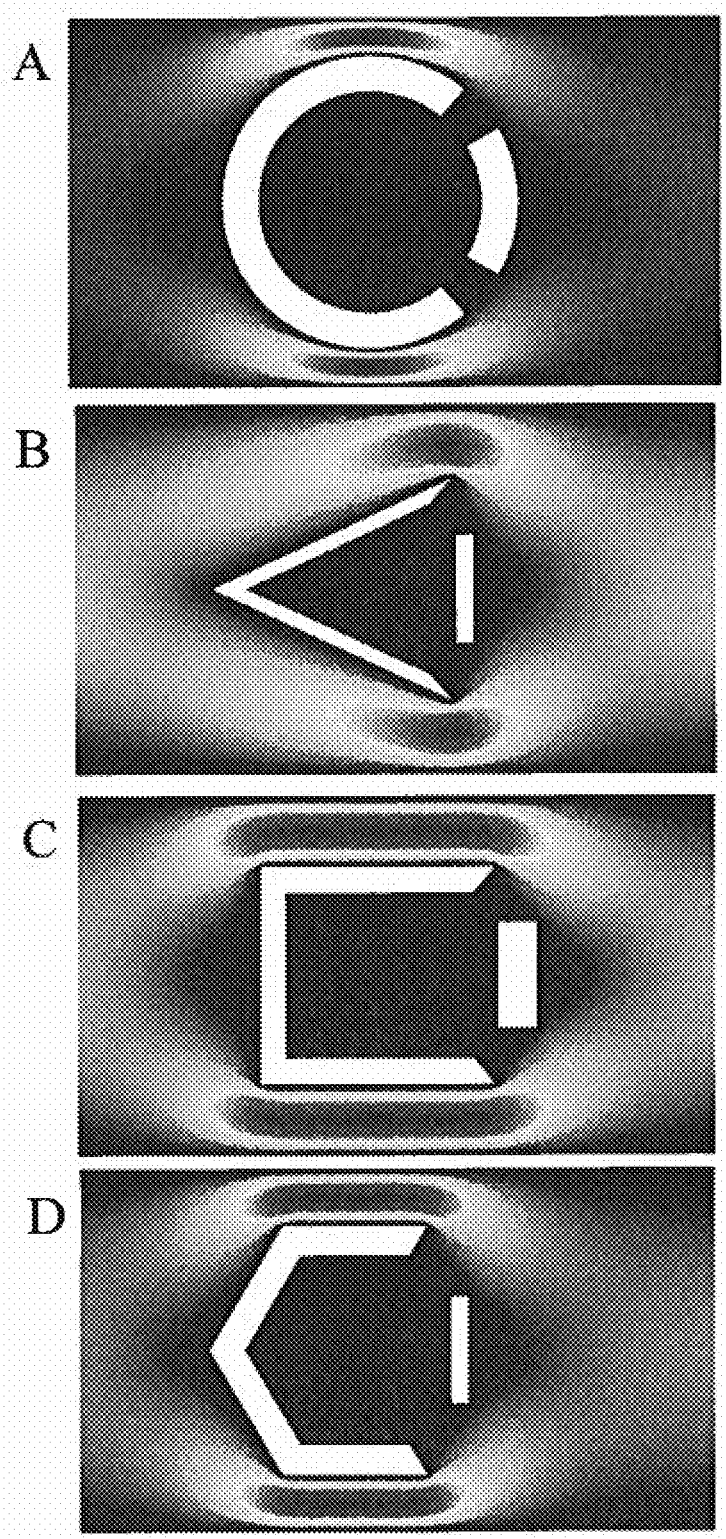
FIGs. 3A-D

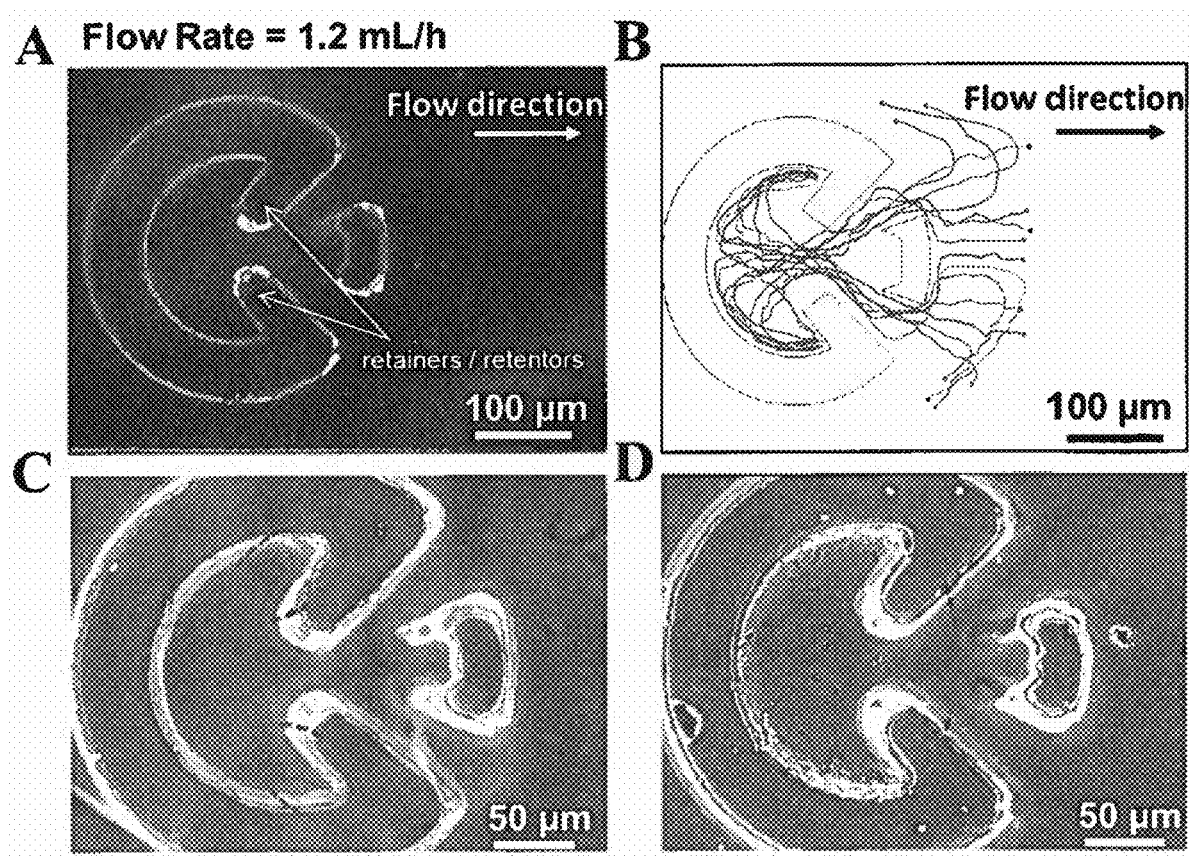
FIGs. 4A-D

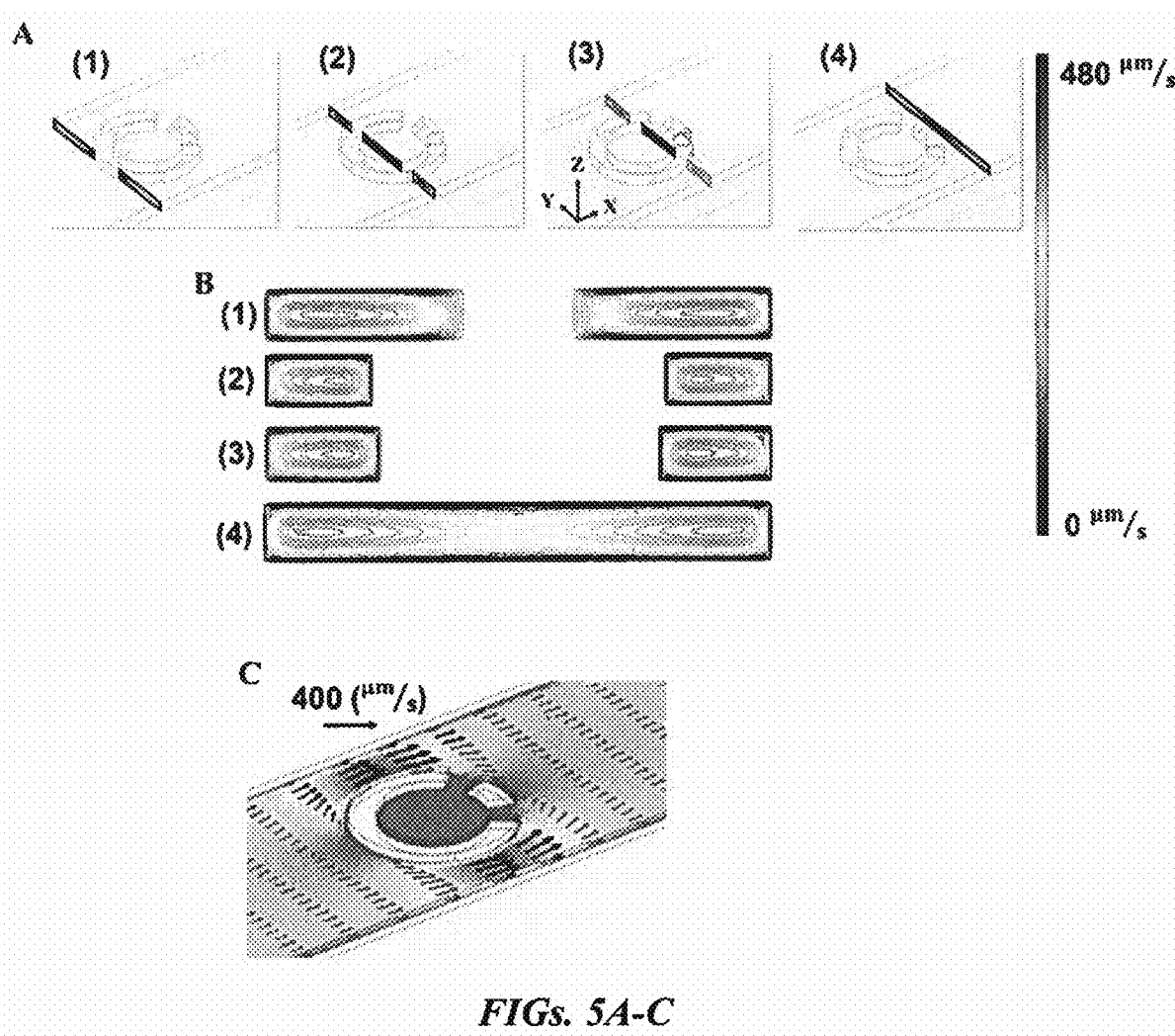
FIGs. 5A-C

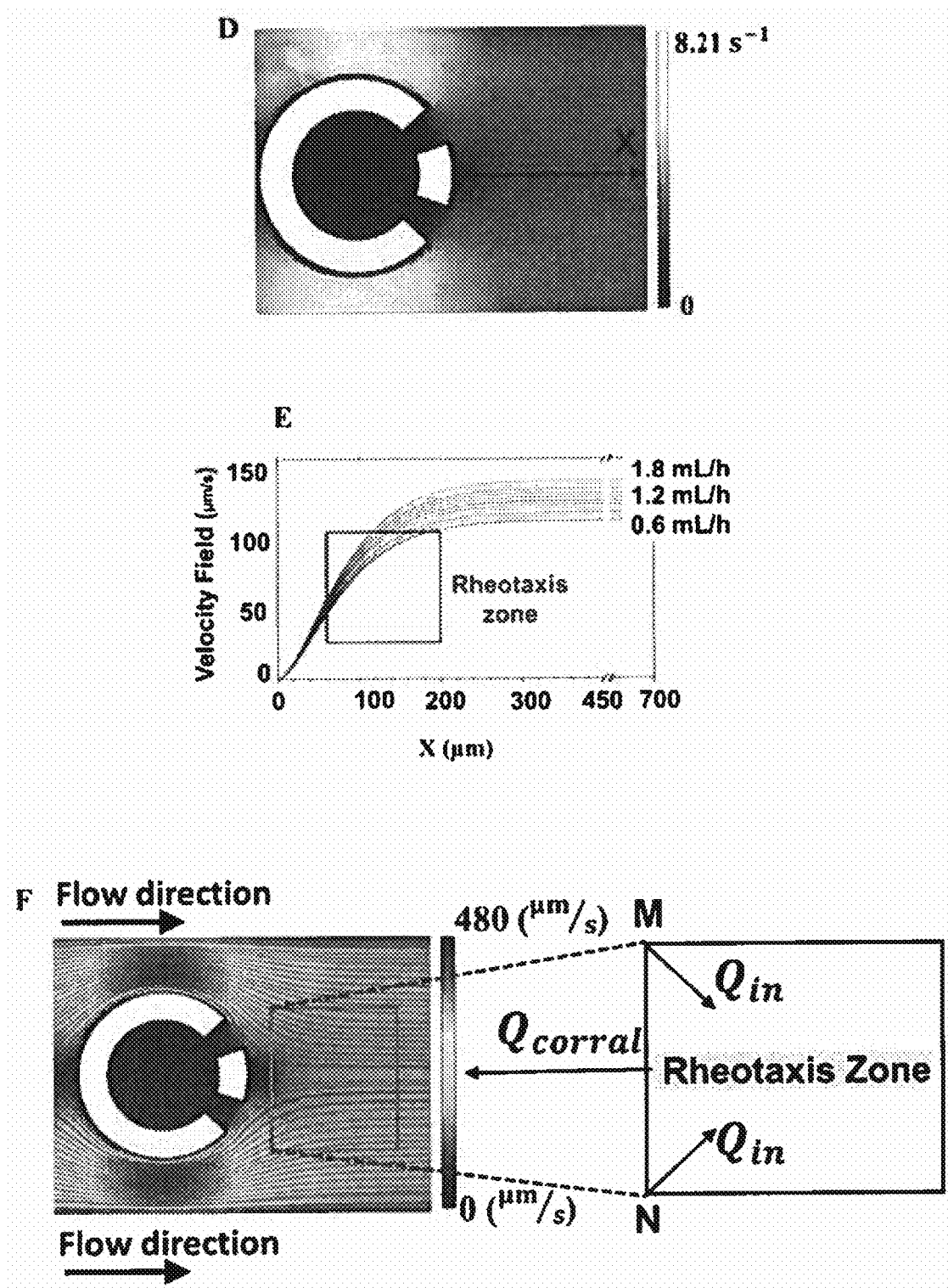
FIGs. 5D-F

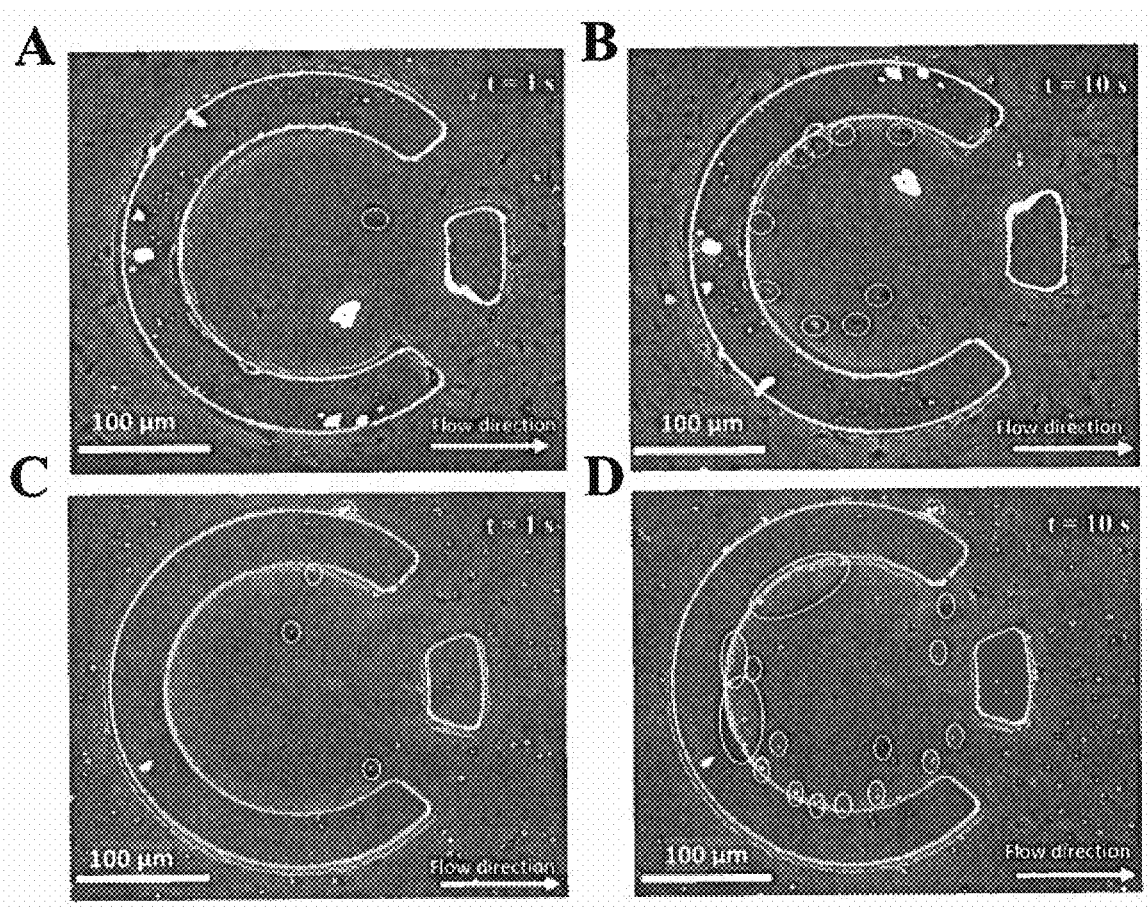
FIGs. 6A-D

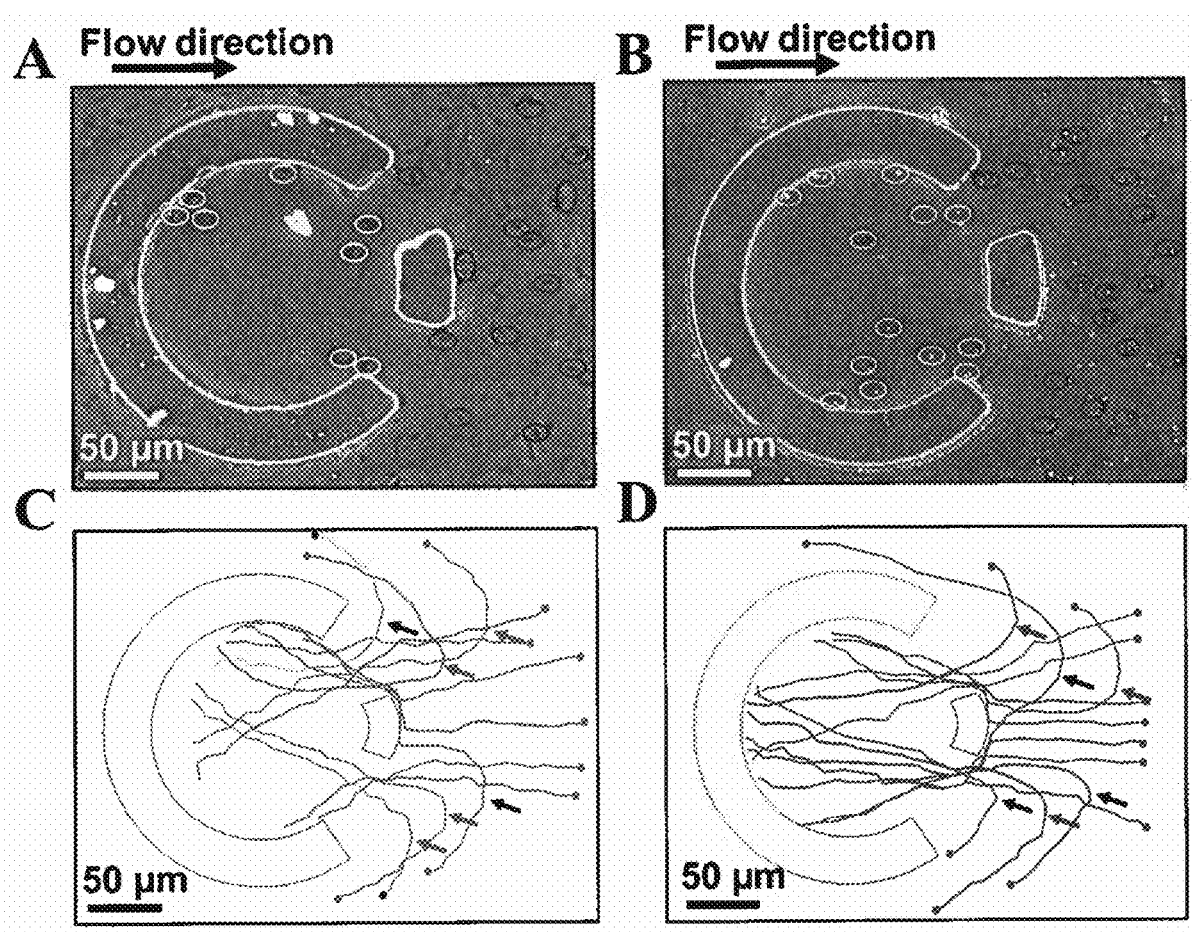
FIGs. 7A-D

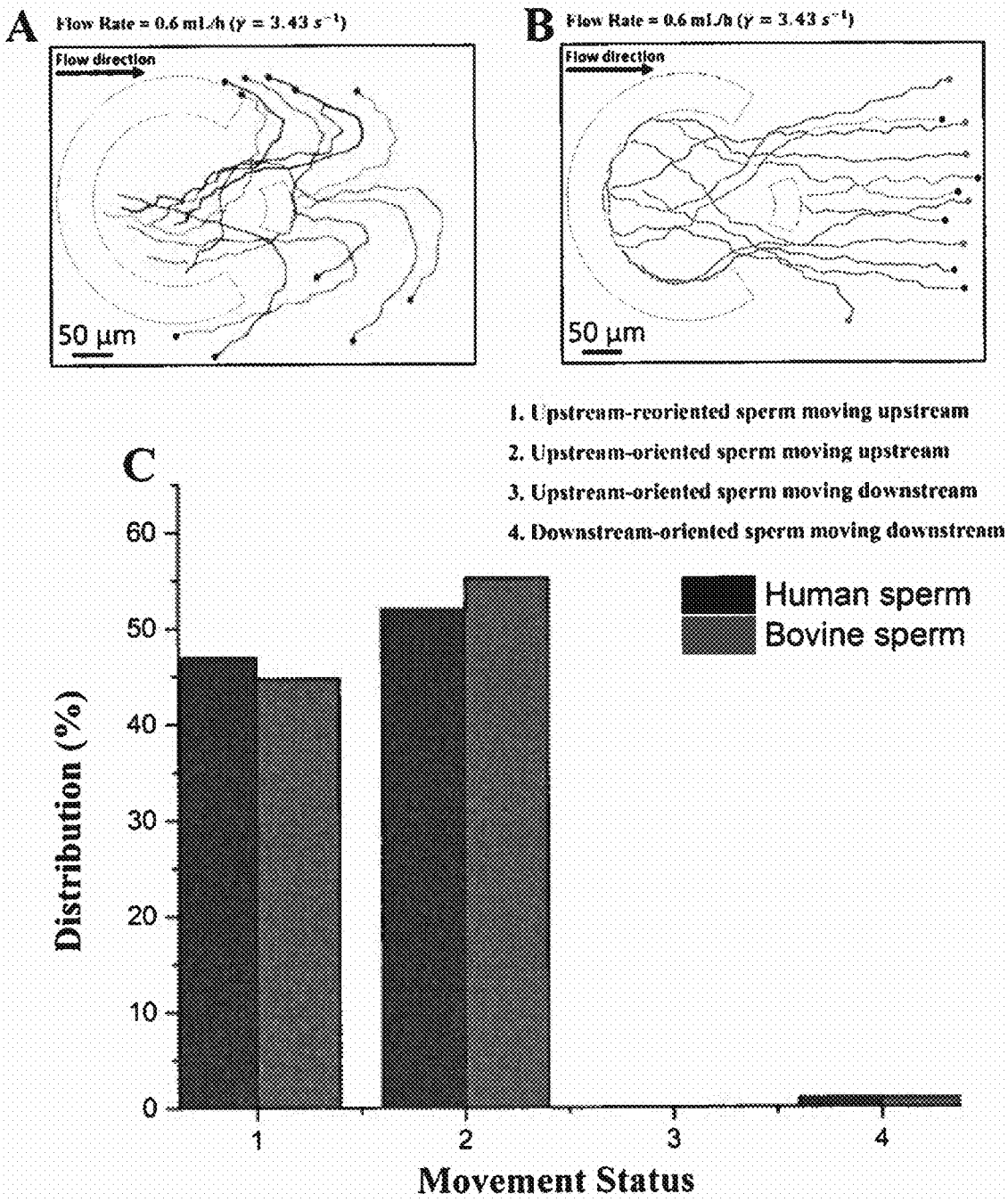
FIGs. 8A-C

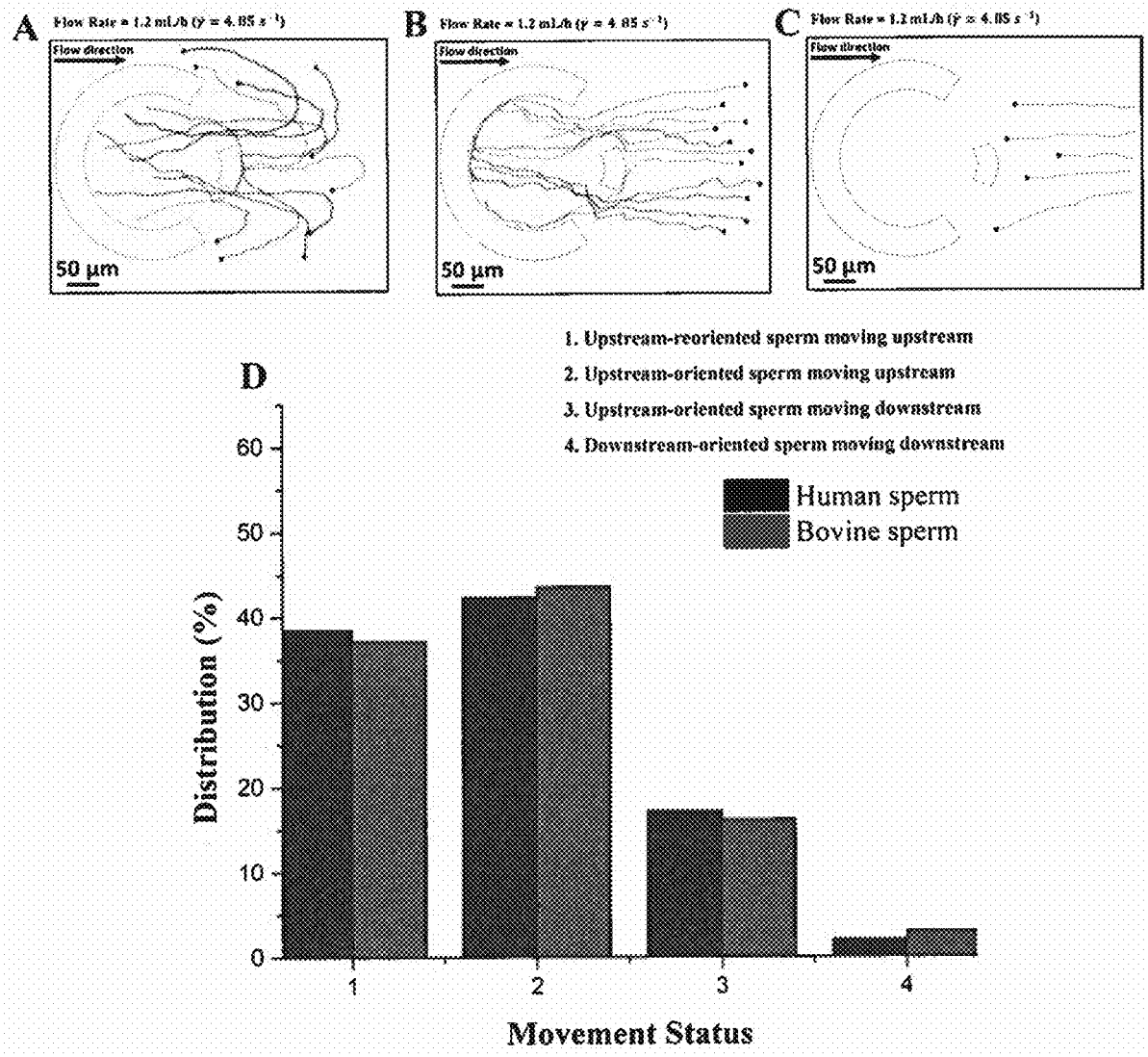
FIGs. 9A-D

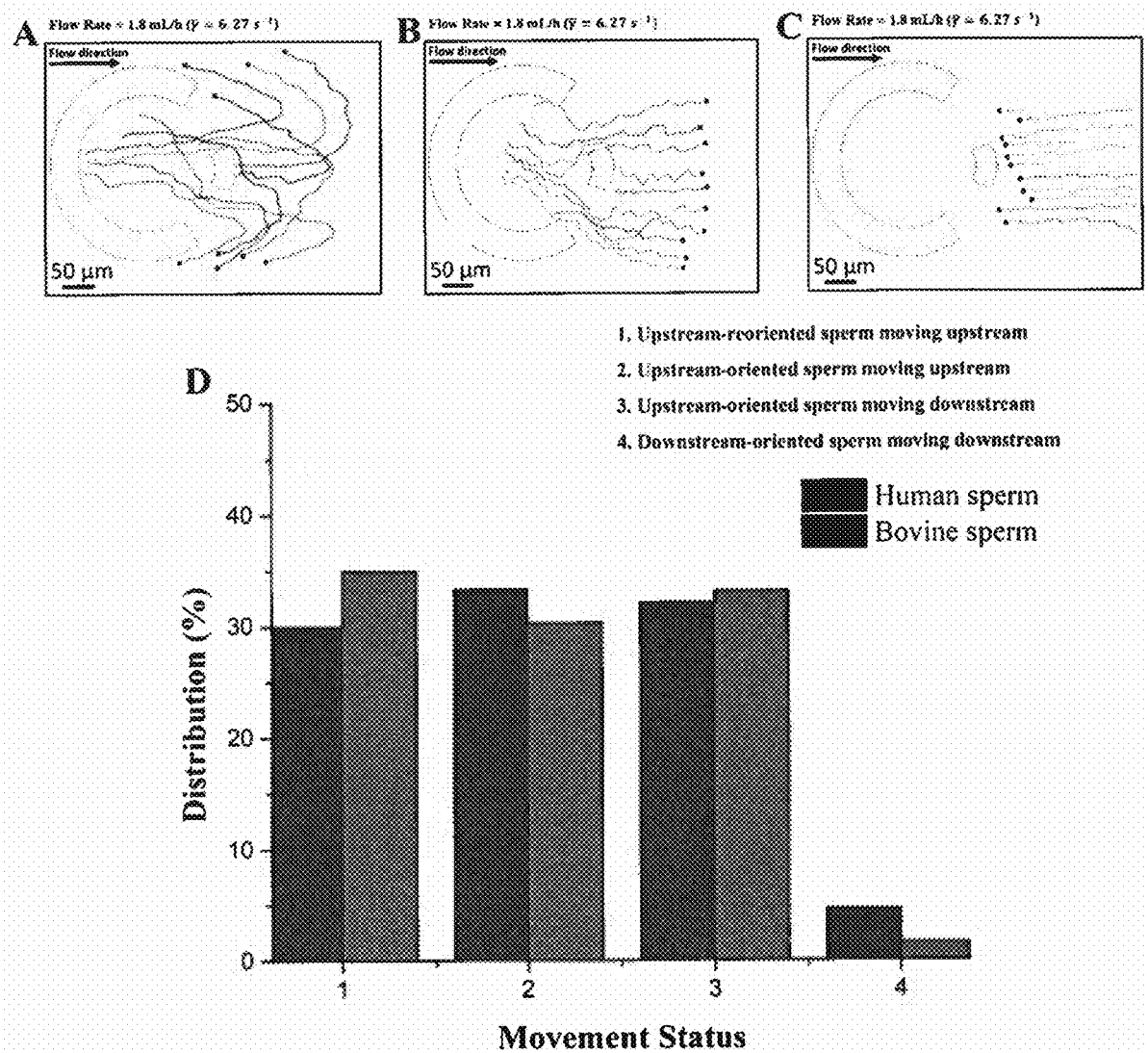
FIGs. 10A-D

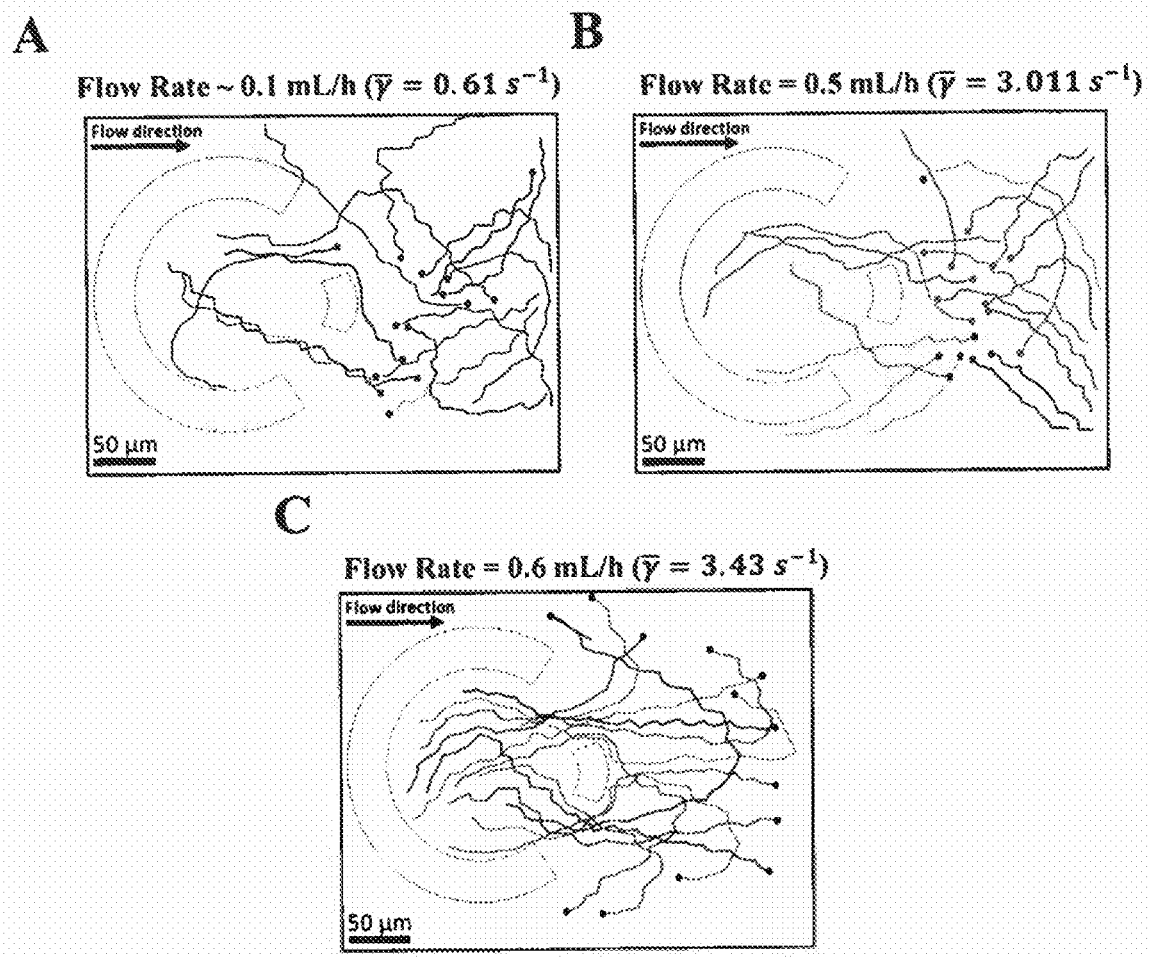
FIGs. 12A-C

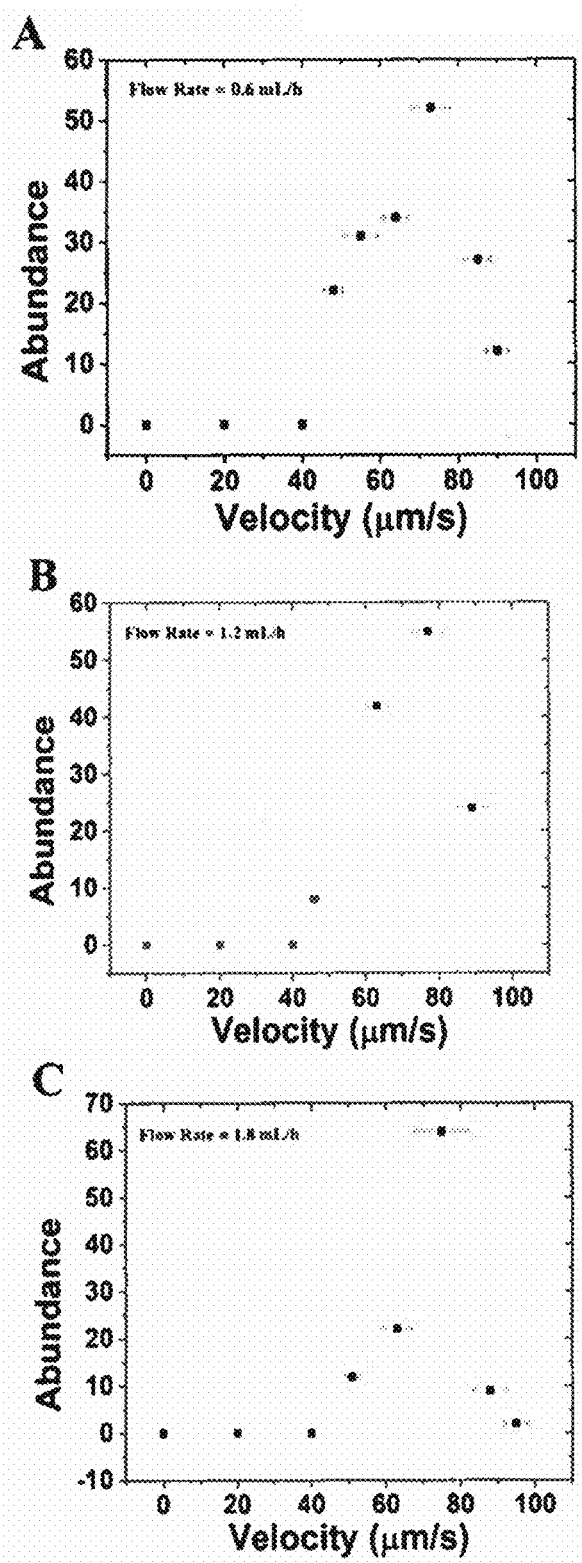
FIGs. 13A-C

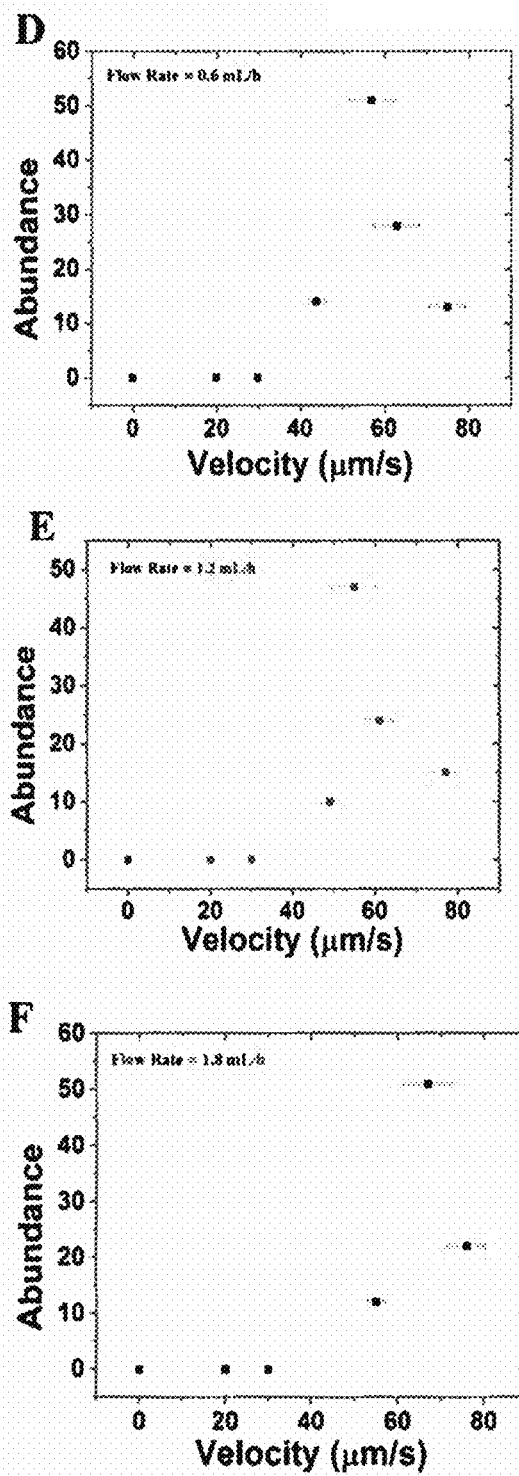
FIGs. 13D-F

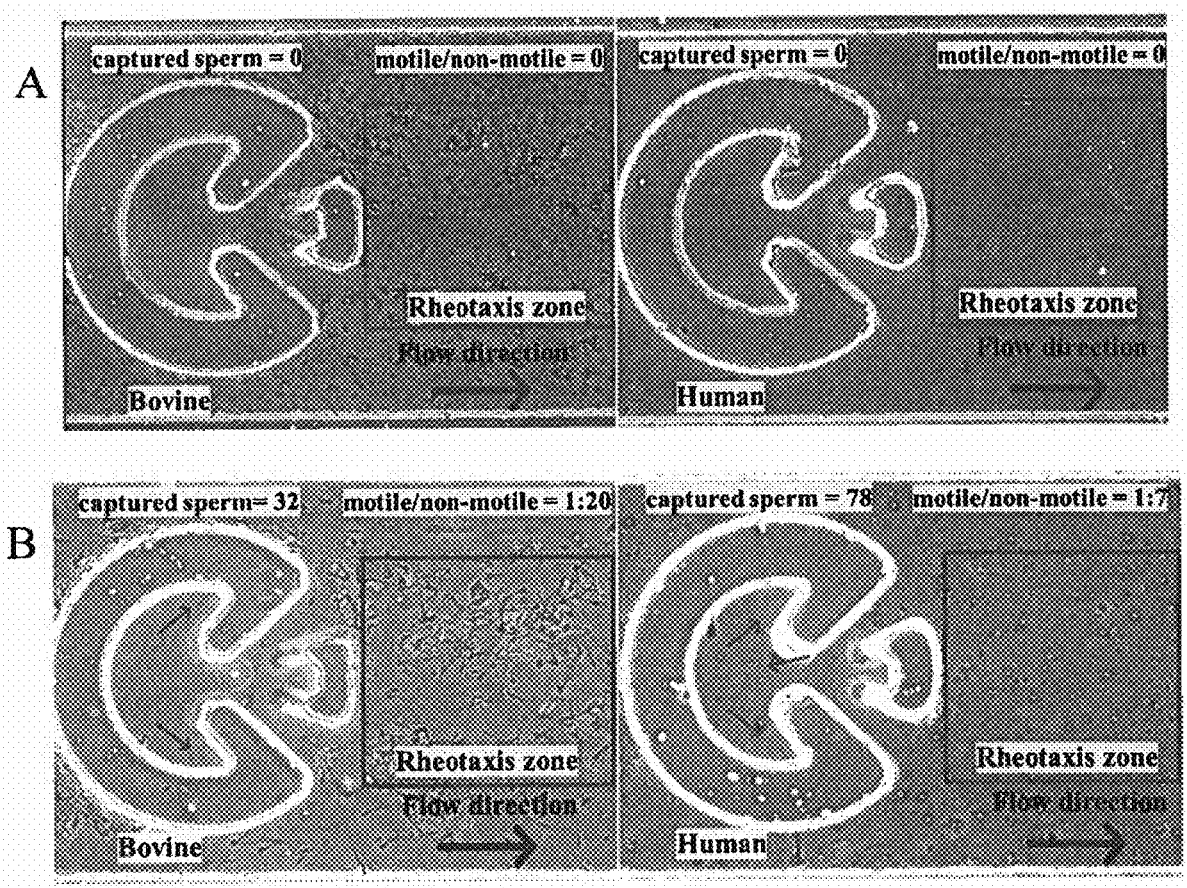
FIGs. 14A-B

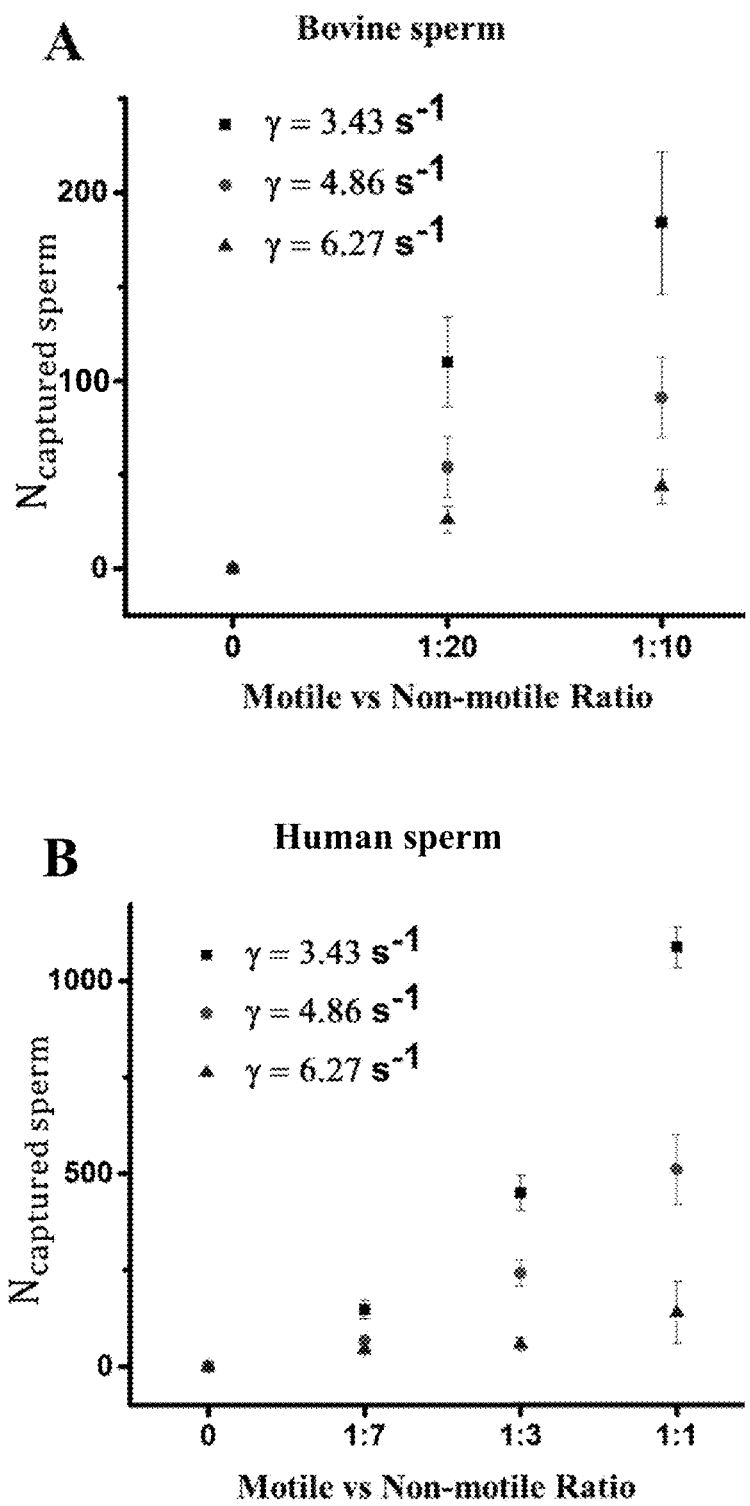
FIGs. 15A-B

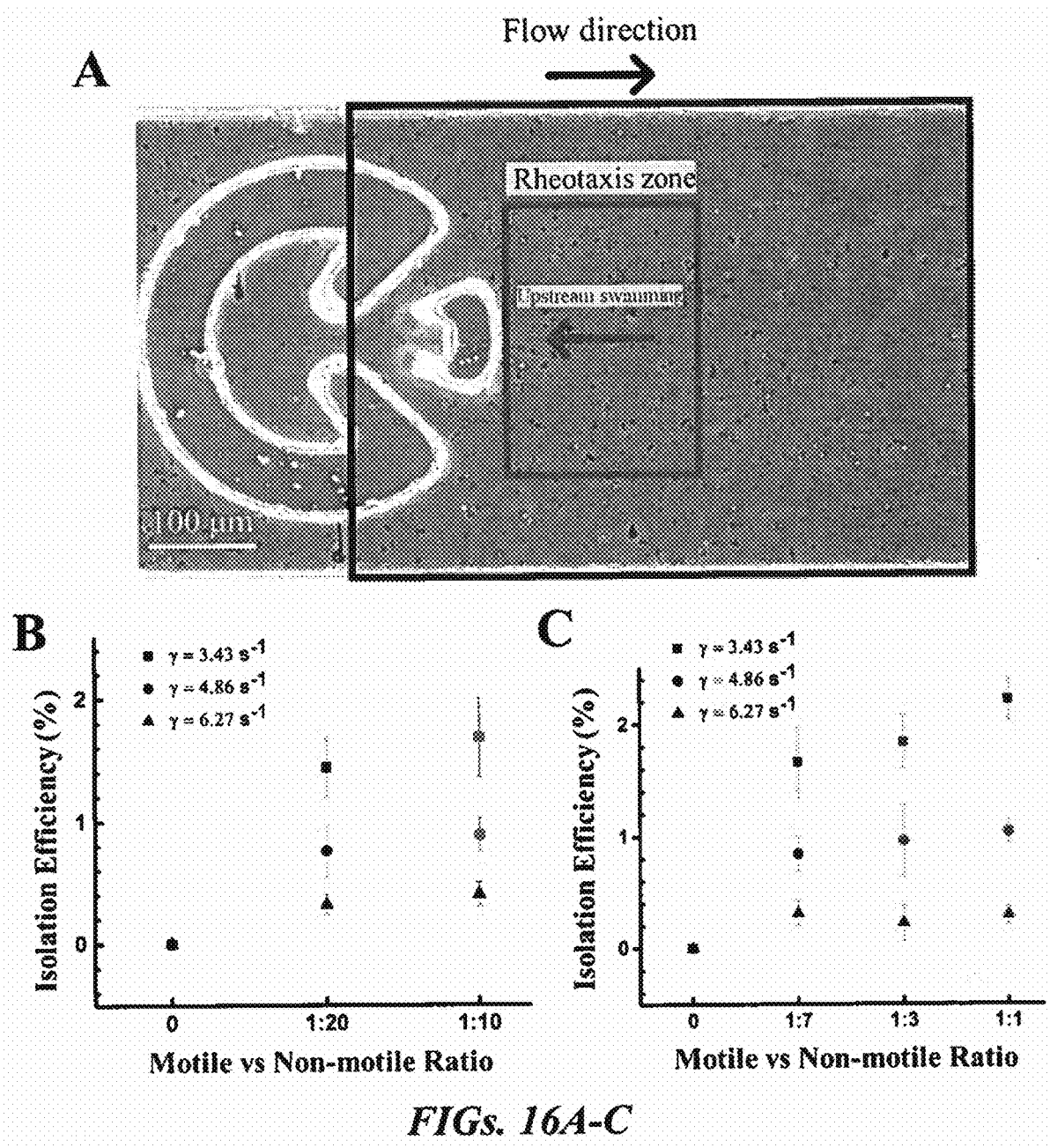
FIGs. 16A-C

RHEOTAXIS-BASED SEPARATION OF MOTILE SPERM AND BACTERIA USING A MICROFLUIDIC CORRAL SYSTEM

This application is a continuation of U.S. patent application Ser. No. 16/374,529, filed Apr. 3, 2019, which claims the benefit of U.S. Provisional Patent Application Ser. No. 62/654,976, filed Apr. 9, 2018, which is hereby incorporated by reference in its entirety.

FIELD

The present application relates to a microfluidic system and method of use of the microfluidic system for separation of motile sperm from immotile sperm or motile bacteria from immotile bacteria.

BACKGROUND

Sperm motility is required for sperm to traverse the female genital tract, reach the site of fertilization, and penetrate the cumulus extracellular matrix around the oocyte and zona pellucida (Suarez et al., "Sperm Transport in the Female Reproductive Tract," Hum Reprod Update 12(1):23-37 (2006); Tulsiani, D., "Introduction to Mammalian Reproduction," Springer Science & Business Media (2012)). According to clinical reports, 10% of couples worldwide are infertile (Guzick et al., "Sperm Morphology, Motility, and Concentration in Fertile and Infertile Men," N Engl J Med 345(19):1388-1393 (2001); Alvarez et al., "Centrifugation of Human Spermatozoa Induces Sublethal Damage; Separation of Human Spermatozoa From Seminal Plasma by a Dextran Swim-Up Procedure Without Centrifugation Extends Their Motile Lifetime," Hum Reprod 8(7):1087-1092 (1993)), and almost half of these infertility cases are due to male infertility as a result of low sperm motility (Tulsiani, D., "Introduction to Mammalian Reproduction," Springer Science & Business Media (2012)). Assisted reproductive technologies (ARTs), such as intrauterine insemination, in vitro fertilization, and intracytoplasmic sperm injection, are used clinically to overcome infertility. All of these infertility treatments include an initial step of separating motile sperm with acceptable morphology from the semen sample. There is some evidence that improvement in the quality of collected sperm can increase the likelihood of successful insemination (Yanagida et al., "Successful Fertilization and Pregnancy Following ICSI and Electrical Oocyte Activation," Hum Reprod 14(5):1307-1311 (1999); Parrish et al., "Effect of Bovine Sperm Separation by Either Swim-Up or Percoll Method on Success of In Vitro Fertilization and Early Embryonic Development," Theriogenology 44(6):859-869 (1995)).

Two methods currently exist for the separation of sperm with desirable motility characteristics, including swim-up and density gradient centrifugation. However, these techniques are time- and labor-intensive. Furthermore, they are not wholly selective, isolating abnormal as well as desirable motile sperm (Guzick et al., "Sperm Morphology, Motility, and Concentration in Fertile and Infertile Men," N Engl J Med 345(19):1388-1393 (2001); Parrish et al., "Effect of Bovine Sperm Separation by Either Swim-Up or Percoll Method on Success of In Vitro Fertilization and Early Embryonic Development," Theriogenology 44(6):859-869 (1995); Kimura et al., "Intracytoplasmic Sperm Injection in the Mouse," Biol Reprod 52(4):709-720 (1995)). The sperm swim-up method requires the semen sample to be centrifuged (200-400 g), which is hazardous to sperm morphology and has a relatively low-yield (Cho et al., "Passively Driven Integrated Microfluidic System for Separation of Motile Sperm," Anal Chem 75(7):1671-1675 (2003)). Density gradient centrifugation exposes semen samples to even greater centrifugal force as well as free-radical mediated DNA damage, which may threaten paternal content and be hazardous to the morphology of the sperm cell (Alvarez et al., "Centrifugation of Human Spermatozoa Induces Sublethal Damage; Separation of Human Spermatozoa From Seminal Plasma by a Dextran Swim-Up Procedure Without Centrifugation Extends Their Motile Lifetime," Hum Reprod 8(7):1087-1092 (1993); Aitken et al., "Significance of Reactive Oxygen Species and Antioxidants in Defining the Efficacy of Sperm Preparation Techniques," J Androl 9(6):367-376 (1988); Friedrich et al., "Chemotaxis of Sperm Cells," Proc Natl Acad Sci 104(33):13256-13261 (2007)).

The development of methods to isolate motile sperm, especially methods that circumvent centrifugation, would benefit infertility treatments and improve our understanding of sperm biology. The factors that influence the journey of a sperm cell, which starts with ejaculation and ends with egg fertilization, are poorly characterized. Some efforts have investigated the response of sperm to external stimuli, like chemical gradients and fluid flow; responses that are generally referred to as "taxis" (Friedrich et al., "Chemotaxis of Sperm Cells," Proc Natl Acad Sci 104(33):13256-13261 (2007); Miki et al., "Rheotaxis Guides Mammalian Sperm," Curr Biol 23(6):443-452 (2013)). Researchers have also investigated the tail beating patterns of sperm in different situations (Suarez et al., "Hyperactivated Motility in Sperm," Reprod Domest Anim 38(2):119-124 (2003); Suarez, S. S., "Hyperactivated Motility in Sperm," J Androl 17(4):331-335 (1996); Suarez, S. S., "Mammalian Sperm Interactions with the Female Reproductive Tract," Cell Tissue Res 363(1):185-194 (2016)), as well as the molecular interactions between sperm and the female reproductive tract (Suarez et al., "Sperm Transport in the Female Reproductive Tract," Hum Reprod Update 12(1):23-37 (2006); Wassarman et al., "Towards the Molecular Basis of Sperm and Egg Interaction During Mammalian Fertilization," Cells Tissues Organs 168(1-2):36-45 (2001); Suarez, S. S., "Mammalian Sperm Interactions with the Female Reproductive Tract," Cell Tissue Res 363(1):185-194 (2016); Eisenbach et al., "Sperm Guidance in Mammals—An Unpaved Road to the Egg," Nat Rev Mol Cell Biol 7(4) (2006)). However, since the study of sperm in vivo is complicated by the existence of many environmental variables, such as pH, chemical gradients, and fluid flow (Tulsiani, D., "Introduction to Mammalian Reproduction," Springer Science & Business Media (2012); Friedrich et al., "Chemotaxis of Sperm Cells," Proc Natl Acad Sci 104(33):13256-13261 (2007); Miki et al., "Rheotaxis Guides Mammalian Sperm," Curr Biol 23(6):443-452 (2013)), many questions about sperm behavior remain unanswered. The concurrent existence of these variables impedes our ability to gain better insight into sperm motion itself, which is a complex topic (Denissenko et al., "Human Spermatozoa Migration in Microchannels Reveals Boundary-Following Navigation," Proc Natl Acad Sci 109(21):8007-8010 (2012)). Thus, the isolation of motile sperm in vitro (eliminating all external hydrodynamic velocity fields and dead sperm), could further assist the study of sperm locomotion. Additionally, isolating sperm in a particular region would enable the evaluation of an individual sperm's biological and physiological responses to a specific chemical or physical factor (Seo et al., "Development of Sorting, Aligning, and Orienting Motile Sperm Using Microfluidic Device Operated by Hydrostatic Pressure," *Microfluid Nanofluidics* 3(5):561-570 (2007)). To summarize, any improvement towards separation and/or isolation of motile sperm from the rest of the semen sample would be an achievement in facilitating the study of mammalian reproduction.

Microfluidic systems are promising tools of fluid manipulation, which could be used to successfully separate and analyze sperm (Koh et al., "The Study of Spermatozoa and Sorting in Relation to Human Reproduction," *Microfluid Nanofluidics* 18(5-6):755-774 (2015)). With exquisite precision at small scales (2 μm-1 mm), microfluidics can enable the manipulation of microswimmers (i.e., microorganisms that swim using a flagella) more easily compared to traditional methods and with fewer drawbacks, as no centrifugal force is required. Additional advantages include low sample consumption and the capability of automation. Recently developed microfluidic technology has been applied to investigate the physical aspects of sperm locomotion and chemotaxis. One such device guides sperm in a counterclockwise direction in a "one-way street" to investigate the effects of structural changes of the microfluidic device on sperm movement (Denissenko et al., "Human Spermatozoa Migration in Microchannels Reveals Boundary-Following Navigation," *Proc Natl Acad Sci* 109(21):8007-8010 (2012)). Other papers have investigated the inclination of sperm to swim near rigid boundaries (Li et al., "Accumulation of Microswimmers Near a Surface Mediated by Collision and Rotational Brownian Motion," *Phys Rev Lett* 103(7):78101 (2009); Tung et al., "Emergence of Upstream Swimming via a Hydrodynamic Transition," *Phys Rev Lett* 114(10):108102 (2015); Zottd et al., "Nonlinear Dynamics of a Microswimmer in Poiseuille Flow," *Phys Rev Lett* 108(21):218104 (2012); Nosrati et al., "Two-Dimensional Sither Swimming of Sperm Within a Micrometre of a Surface," *Nat Commun* 6:8703 (2015); Tung et al., "Microgrooves and Fluid Flows Provide Preferential Passageways for Sperm Over Pathogen Tritrichomonas Foetus," *Proc Natl Acad Sci* 112(17):5431-5436 (2015)), and another experimental study has provided a theoretical model for the rheotactic behavior of sperm (Bukatin et al., "Bimodal Rheotactic Behavior Reflects Flagellar Beat Asymmetry in Human Sperm Cells," *Proc Natl Acad Sci* 112(52):15904-15909 (2015)), i.e., their proclivity to swim in the opposite direction of the surrounding fluid flow (Elgeti et al., "Physics of Microswimmers—Single Particle Motion and Collective Behavior: A Review," *Reports Prog Phys* 78(5):56601 (2015)).

In the last decade, some microfluidic devices have been proposed for ART applications (Smith et al., "Application of Microfluidic Technologies to Human Assisted Reproduction," *MHR Basic Sci Reprod Med* 23(4):257-268 (2017); Tasoglu et al., "Exhaustion of Racing Sperm in Nature—Mimicking Microfluidic Channels During Sorting," *Small* 9(20):3374-3384 (2013); Nosrati et al., "Microfluidics for Sperm Analysis and Selection," *Nat Rev Urol* (2017)), including those that have been used to separate sperm (Schuster et al., "Isolation of Motile Spermatozoa From Semen Samples Using Microfluidics," *Reprod Biomed Online* 7(1):75-81 (2003)). In one effort, a passive microfluidic system called MISS was proposed that could separate motile sperm from the rest of the sample (Cho et al., "Passively Driven Integrated Microfluidic System for Separation of Motile Sperm," *Anal Chem* 75(7):1671-1675 (2003)). Although the motility of the separated sample using this device was reported as ~100%, the presence of sperm with non-progressive and abnormal motility in the separated fraction lowers the effectiveness of this technique. Additionally, the device provides no tunability to modify the motility distribution of the separated sperm, demonstrating the technique's low precision. Active microfluidic methods have also been reported (Seo et al., "Development of Sorting, Aligning, and Orienting Motile Sperm Using Microfluidic Device Operated by Hydrostatic Pressure," *Microfluid Nanofluidics* 3(5):561-570 (2007); Modak et al., "Cell Separation in a Microfluidic Channel Using Magnetic Microspheres," *Microfluid Nanofluidics* 6(5):647 (2009); Devenica et al., "Progress on an Optical Trapping Assay to Measure DNA Folding Pathways in Sperm," *Optical Trapping and Optical Micromanipulation XIV* p 103472V (2017)), in which external active forces, such as hydrostatic pressure, optical traps, and magnetophoresis, are used for sperm separation. However, these techniques are not suitable for the isolation of healthy sperm (Cho et al., "Passively Driven Integrated Microfluidic System for Separation of Motile Sperm," *Anal Chem* 75(7):1671-1675 (2003)), being too invasive. In addition, complex experimental setups are required for these active methods, making them time and labor intensive.

The present application is directed to overcoming the deficiencies in the art.

SUMMARY

The present application relates to a microfluidic system for separation of motile sperm from immotile sperm or motile bacteria from immotile bacteria. The system includes a housing having a first end, and a second end, and containing a passage connecting the first and second ends. There is an inlet at the first end of the housing for charging fluids into the passage proximate to the first end of said housing. There is an outlet at the second end of said housing for discharging fluids from the passage proximate to the second end of said housing, where fluid flows from the inlet, through the passage, and into the outlet. There are one or more corrals within the passage, each of the corrals including a closed side and a partially open side. The closed side of the corrals is closer to the first end than the partially open side, with the closed side and partially open side defining between them a confinement region suitable for retaining motile sperm or motile bacteria.

A second aspect of the present application relates to a method for separation of motile sperm from immotile sperm or motile bacteria from immotile bacteria. The method includes providing the microfluidic system of the present application, providing a sperm-containing sample or a bacteria-containing sample, and passing the sperm-containing sample or the bacteria-containing sample through the inlet, through the passage, and through the outlet of the microfluidic system. The motile sperm or motile bacteria are retained within the one or more corrals, while immotile sperm or immotile bacteria are discharged through the outlet.

The microfluidic device can noninvasively and passively separate motile sperm from the rest of the semen sample in a precise and tunable manner. This design relies on the rheotactic behavior of sperm. Employing this device, the isolation of motile human and bovine sperm in a corral-shaped feature inside the microfluidic channel is demonstrated. To establish a rheotaxis zone in front of the corral, where only sperm with normal and progressive motility are able to swim upstream and thus enter the structure, finite element method (FEM) simulations were performed to determine appropriate injection rates of the sperm medium. Moreover, a minimum shear rate within the rheotaxis zone required for sperm to reorient upstream was experimentally measured. Subsequently, it was demonstrated that this new separation method provides enhanced precision in sperm selection by experimentally extracting the sperm movement distribution within the rheotaxis zone, measuring the velocity distribution of the captured sperm, and proposing a theoretical model for sperm motion within this zone. This new separation method is highly tunable in regards to the motility of the isolated sample, providing marked improvement in comparison to established sperm isolation methods. No dead sperm or sperm with abnormal motility were observed within the corral. Thus, 100% of the separated sperm exhibit normal and progressive motility, which is an unprecedented advantage of this separation technique. Finally, by designing and incorporating sperm retainers inside the corral, the device is made more stable, increasing the residence time of the sperm from ~12 s to more than 45 minutes.

By taking advantage of the rheotactic behavior of sperm, this novel microfluidic device is able to corral motile sperm with progressive velocities in the range of 48-93 μm/s and 51-82 μm/s for bovine and human samples, respectively. More importantly, the separated fractions of both human and bovine samples feature 100% normal progressive motility. Furthermore, by extracting the sperm swimming distribution within the rheotaxis zone and sperm velocity distribution inside the corral, the minimum velocity of the corralled sperm can be adjusted by changing the flow rate. Therefore, it is possible to control the motility of the separated sample. This microfluidic device is simple to use, robust, and has a high throughput compared to traditional methods of motile sperm separation, fulfilling the needs for sperm sample preparation for medical treatments, clinical applications, and fundamental studies.

The separation of motile sperm from semen samples is required for medical infertility treatments and clinical studies. Conventional methods are time and labor intensive and could be potentially hazardous to morphology and paternal content of the sperm. Using the microfluidic corral system of the present application and the ability of viable sperm to swim against flow, the passive isolation of motile sperm from the semen sample inside a corral is accomplished. This device can separate sperm with velocities higher than a cut off, which is tunable with the injection rate. The unprecedented efficiency of the device of the present application in comparison with previous studies, and its benign passive nature, make it favorable for sperm separation.

In this application the inventors demonstrate a high-throughput microfluidic device that can passively isolate motile sperm within corrals inside a fluid channel, separating them from the rest of the diluted sample. Using finite element method simulations and proposing a model for sperm motion, it was investigated how flow rate can provide a rheotaxis zone in front of the corral for sperm to move upstream/downstream depending on their motility. Using three different flow rates that provided shear rates above the minimum value within the rheotaxis zone, the device was experimentally tested with human and bovine semen. By taking advantage of the rheotactic behavior of sperm, this novel microfluidic device is able to corral motile sperm with progressive velocities in the range of 48-93 μm/s and 51-82 μm/s for bovine and human samples, respectively. More importantly, the separated fractions of both human and bovine samples feature 100% normal progressive motility. Furthermore, by extracting the sperm swimming distribution within the rheotaxis zone and sperm velocity distribution inside the corral, the minimum velocity of the corralled sperm can be adjusted by changing the flow rate. That is, it is possible to control the motility of the separated sample. This microfluidic device of the present application is simple to use, robust, and has a high throughput compared to traditional methods of motile sperm separation, fulfilling the needs for sperm sample preparation for medical treatments, clinical applications, and fundamental studies.

BRIEF DESCRIPTION OF THE DRAWINGS

FIGS. 1A-C are illustrations showing the minimal hydrodynamic model for the upstream orientation of sperm. FIG. 1A shows a PDMS-based microfluidic device featuring 7 corrals inside the channel. FIG. 1B is a side view of the sperm in vicinity of the top surface. The sperm tail experiences a greater force than its head. FIG. 1C is a top view of a sperm showing the rotation caused by shear which leads to upstream orientation. $F_p$ is the propulsive force produced by flagellum movement.

FIG. 2 is an illustration of three different sized corrals of the present application.

FIGS. 3A-D show examples of different corral shapes that can be used in the present application.

FIGS. 4A-D show enhanced sperm retention using a modified corral structure. FIG. 4A is the microfluidic corral device with sperm retainers. FIG. 4B shows the trajectories extracted for human sperm entering the corral. All the sperm remained inside the corral by being captured in the corners or following the interior walls of the retainers. For FIG. 4B, all trajectories begin at the black filled-in circles. FIG. 4C shows a bovine semen sample that was injected into the microfluidic system of the present application. The motile sperm entered the corral and remained inside. FIG. 4D shows a human semen sample that was injected into the microfluidic system of the present application, and the corral captured and maintained the motile sperm.

FIGS. 5A-G show the simulation-based velocity field of the sperm medium and trajectories extracted for sperm inside the rheotaxis zone. FIG. 5A is a velocity field of the semen sample medium is calculated and presented in four different Y-Z cut planes. FIG. 5B shows the velocity fields of the Y-Z cut planes drawn in contour levels. FIG. 5C is an illustrative velocity field around the corral at an injection rate of 1.2 mL/h in an X-Y cut plane. FIG. 5D shows the shear rate in the vicinity of the top surface around the corrals. FIG. 5E is a graphical illustration of the velocity field of the sperm medium along the X axis. FIG. 5F displays the rheotaxis zone in front of the corral. The medium velocity field and shear rate in the zone is calculated by FEM simulations. This zone is a hypothetical area in front of the corral in which sperm entering it are likely to enter the corral. The sperm enter the rheotaxis zone from points M and N with $Q_{in}$. A portion of these sperm will enter the corral at the rate of $Q_{corral}$. FIG. 5G are the graphical illustrations of the equations of sperm motion solved for 400 sperm with velocities between 40-90 μm/s following a normal distribution with a mean value of 65 μm/s. As the flow/shear rate increases, the number of sperm moving upstream toward the corral ($Q_{corral}$) drops.

FIGS. 6A-D are images of the dynamic of isolated bovine and human sperm within the corral as a function of time. FIG. 6A shows at t=1 s, a single bovine sperm enters the corral. FIG. 6B shows at t=10 s, the number of isolated bovine sperm has increased to 10 and all of them swim due to their own propulsion. FIG. 6C shows at t=1 s, three human sperm have entered the corral. FIG. 6D shows at t=10 s, almost 40 human sperm have been captured within the corral.

FIGS. 7A-D show sperm undergoing rheotaxis in bovine and human samples. FIG. 7A show sperm with upstream swimming behavior prior to isolation in the bovine sample being detected and indicated with black ovals whereas the isolated sperm are indicated with white ovals. FIG. 7B are similarly labeled sperm in the human sample with black and white ovals to indicate upstream-swimming and isolated sperm, respectively. FIG. 7C shows the trajectories of twenty different sperm in the bovine sample. All trajectories begin at the black filled-in circles. FIG. 7D shows the trajectories of human sperm nearby and inside the corral. In FIGS. 7C-D, the trajectories that show a change in sperm orientation due to rheotaxis are indicated with arrows.

FIGS. 8A-C are graphical representations of the distribution of sperm movement status for an injection rate of 0.6 mL/h. FIG. 8A is an illustration of the trajectories of sperm reoriented upstream. FIG. 8B is an illustration of the trajectories of sperm oriented upstream. For FIGS. 8 A-B, all trajectories begin at the black filled-in circles. FIG. 8C is a graphical representation the distribution of sperm movement status for both human and bovine sperm samples.

FIGS. 9A-D are graphical representations of the distribution of sperm movement status for an injection rate of 1.2 mL/h. FIG. 9A is an illustration of the trajectories of sperm reoriented upstream. FIG. 9B is an illustration of the trajectories of sperm oriented upstream. FIG. 9C is an illustration of the trajectories of sperm oriented upstream but cannot move upstream. For FIGS. 9 A-C, all trajectories begin at the black filled-in circles. FIG. 9D is a graphical representation of the distribution of sperm movement status for both human and bovine sperm samples. The number of sperm moving downstream increased.

FIGS. 10A-D are graphical representations of the distribution of sperm movement status for an injection rate of 1.8 mL/h. FIG. 10A is an illustration of the trajectories of sperm reoriented upstream. FIG. 10B is an illustration of the trajectories of sperm oriented upstream. FIG. 10C is an illustration of the trajectories of sperm oriented upstream but cannot move toward the corral. For FIGS. 10A-C, all trajectories begin at the black filled-in circles. FIG. 10D is a graphical representation of the distribution of sperm movement status for both human and bovine sperm samples. The number of sperm moving downstream but oriented upstream increased.

Figure 1A:
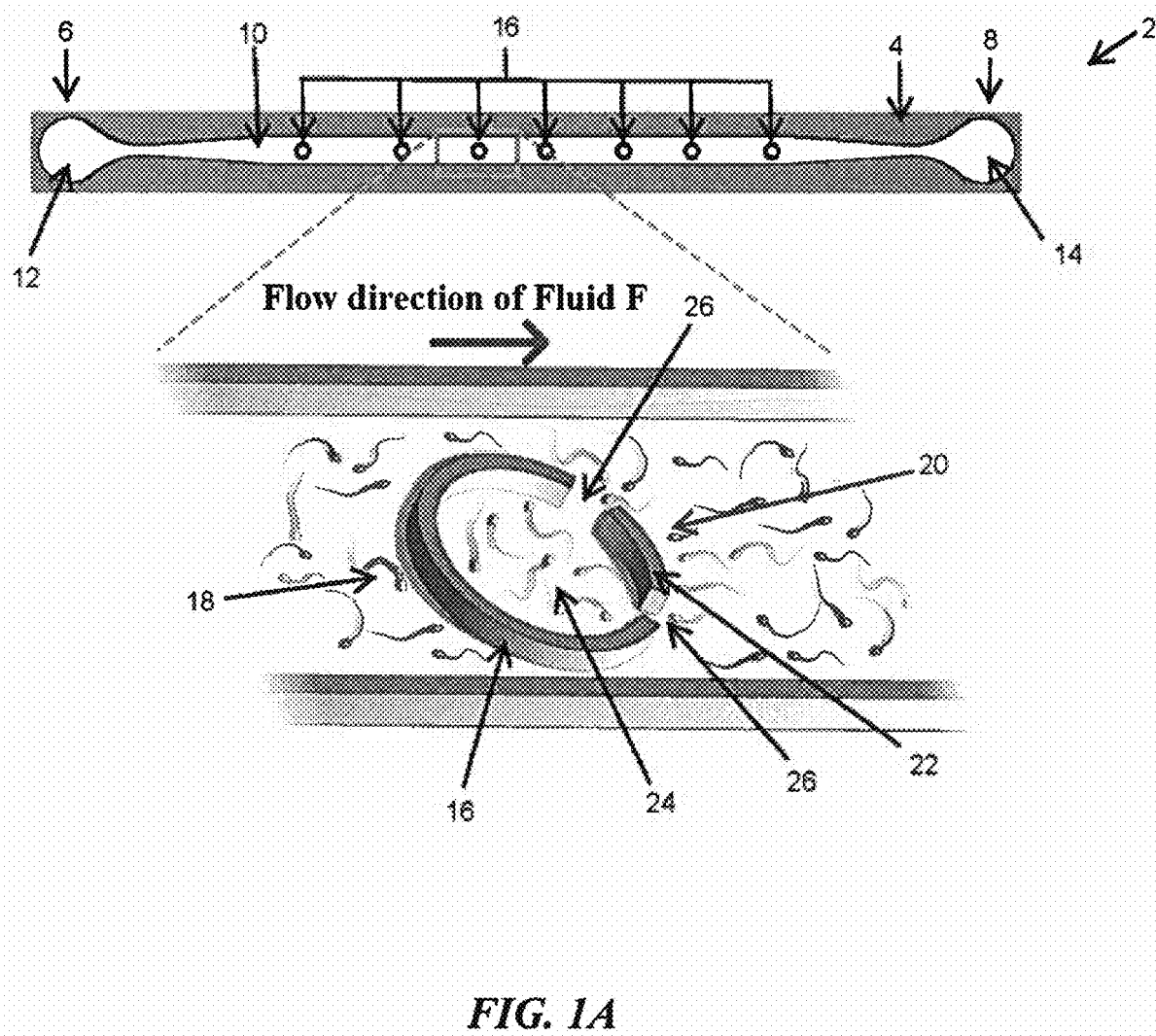

vs. average velocity field within the rheotaxis zone. The model- and experiment-based curves are depicted for both human and bovine samples. As the flow rate increases, the portion of sperm with enough motility to overcome the velocity field of the medium decreases.

FIGS. 12A-C are illustrations of the sperm motility in the determination of the minimum shear rate required for sperm reorientation toward upstream. FIG. 12A is an illustration showing that at a low injection rate (0.1 mL/h) each sperm will move toward its original direction. FIG. 12B is an illustration showing that increasing the flow rate to 0.5 mL/h is not enough for sperm to undergo rheotaxis. FIG. 12C is an illustration showing that once the injection rate was set to 0.6 mL/h, all the sperm started swimming upstream. The corresponding minimum shear rate for this flow rate in the rheotaxis zone was $\gamma_{min}=3.43\pm0.12$ s$^{-1}$, which is reported as the mean value of the calculated shear rates for each reorientation point. For FIGS. 12A-C, all trajectories begin at the black filled-in circles.

FIGS. 13A-F are plots of the velocity distribution of isolated bovine (FIGS. 13A-C) and human (FIGS. 13D-F) sperm within the corral for different flow rates. FIG. 13A is a plot at the minimum injection flow rate of 0.6 mL/h, in which bovine sperm with different velocities from 45 µm/s to 92 µm/s were observed in the corral. The maximum abundance occurs for sperm with velocities of ~75 µm/s. The number of sperm with motilities lower than 40 µm/s was zero. FIG. 13B is a plot of the velocity distribution of isolated bovine sperm at an injection flow rate of 1.2 mL/h. The increasing injection rate appears to reduce the number of low motility sperm captured in the corral. Sperm featuring a motility of ~75 µm/s are still the most abundant. FIG. 13C is a plot of the velocity distribution of isolated bovine sperm at an injection flow rate of 1.8 mL/h, there is a further reduction in the number of low motility bovine sperm. FIG. 13D is a plot of the velocity distribution of human sperm at an injection flow rate of 0.6 mL/h, human sperm with velocities of ~65 µm/s are the most dominant in the separated sample. FIG. 13E shows the velocity distribution of human sperm as the flow rate is increased to 1.2 mL/h, the minimum velocity cutoff also increases, and FIG. 13F shows the minimum cutoff increases to 55 µm/s at a flow rate of 1.8 mL/h. The peak abundance of this velocity distribution occurred for a higher velocity (63.8 µm/s).

FIGS. 14A-B are images of captured sperm inside the corral. FIG. 14A shows that no sperm were captured inside the corral when the injected samples exhibited no motility (motile vs. non-motile ratio=0). FIG. 14B shows that as the motile vs. non-motile ratio increases, viable sperm with normal and progressive motility become captured. Left: bovine sample, Right: human sample.

FIGS. 15A-B are graphs representing the number of sperm captured inside the corral after 5 minutes. FIG. 15A is a graph of the number of captured bovine sperm for samples with different motile vs. non-motile ratios as a function of shear rate within rheotaxis zone. FIG. 15B is a graph of the number of captured human sperm.

FIGS. 16A-C display the efficiency of the corral device of the present application. FIG. 16A is a movie frame selected to evaluate the efficiency of the device of the present application. FIG. 16B is a graphical representation of the efficiency of the corral device of the present application for bovine sperm with three different motile vs. non-motile ratios at three different shear rates. FIG. 16C is a graphical representation of the efficiency of the device of the present application for human sperm with four different motile vs. non-motile ratios at three different shear rates.

DETAILED DESCRIPTION

The present application relates to a microfluidic system for separation of motile sperm from immotile sperm or motile bacteria from immotile bacteria. The system includes a housing having a first end, and a second end, and containing a passage connecting the first and second ends. There is an inlet at the first end of the housing for charging fluids into the passage proximate to the first end of said housing. There is an outlet at the second end of said housing for discharging fluids from the passage proximate to the second end of said housing, where fluid flows from the inlet, through the passage, and into the outlet. There are one or more corrals within the passage, each of the corrals including a closed side and a partially open side. The closed side of the corrals is closer to the first end than the partially open side, with the closed side and partially open side defining between them a confinement region suitable for retaining motile sperm or motile bacteria.

In one embodiment of the present application, the microfluidic system includes a plurality of corrals spaced apart within the passage. These corals can include a wall member located opposite the closed end of the corral to define a pair of openings at opposite ends of the wall member leading to the confinement region. This confinement region can have a maximum interior dimension ranging from about 5 μm to about 2 mm. Furthermore, there is (are) one or more gaps between the closed side and the partially open side of the corrals, with each gap ranging from about 10 μm to about 500 μm As seen in FIG. 1A, the microfluidic system 2, includes housing 4, with first end 6, and second end 8. Connecting first end 6 to second end 8 is passage 10. At first end 6 is located inlet 12 for charging fluids into system 2. At second end 8 is located outlet 14 which allows fluid to pass out of system 2. Passage 10 permits fluid F to flow from inlet 12 to outlet 14. Located in passage 10 are corrals 16, with closed side 18 of the corral being proximate to inlet 12 and partially open side 20 of the corral being proximate to outlet 14. Wall member 22 is located opposite closed side of corral 18, forming confinement region 24 inside of coral 16. Openings (also referred to as gaps) 26, are located on partially open side 20 of the corral. Openings 26 allow for motile cell entry into confinement region 24. Optionally present are retainers (or retentors) to prevent the motile sperm and bacteria from leaving the confinement region (see FIGS. 4A-D).

In accordance with the present application, the corrals have a convex polygonal configuration. In one embodiment, the configuration of the corrals is selected from the group consisting of a C-shaped configuration, a triangular-shaped configuration, a rectangular configuration, a pentagonal configuration, an oval configuration, a square configuration, and a semicircular configuration.

The microfluidic system can be created and used with several corrals with different sizes. Examples of some corrals of different sizes with their potential rheotactic zone are displayed in FIG. 2. In this case, each of these corrals, relying on their size feature different shear rates within the corresponding rheotaxis zone, and thus, smaller corrals capture lower amounts of sperm with narrower range of motility. Whereas the larger corrals capture larger amounts of sperm with wider range of motility.

The idea of a microfluidic corral system is independent of the corral's shape. Although the corral's size may alter the range of motility in the selected sample, the selection mechanism is the same. This may be realized by looking at the flow properties in FIG. 3, which displays corrals of differing shapes with their rehotactic zones. There is a similarity in the flow field behind, near, and in front of the corral as a barrier, regardless of the corral's shape. The sperm between corrals and the walls determine the flow properties throughout the passage including the flow behind, near, and in front of the corral. This independence is due to the swimming of sperm that is solely determined by the flow, and any shape that can proved the flow for sperm to swim upstream is acceptable. In fact, any barrier with any shape that can cause a decay in the flow, can be used as a corral structure.

In one embodiment of the present application, the microfluidic system can have anywhere from 1 to about 100 corrals per system. These corrals can be spaced apart by a distance ranging from about 100 μm to about 1000 μm. Each corral has a maximum exterior dimension of about 80 μm to about 1 mm. Additionally, the corals can have a maximum inner diameter ranging from about 20 μm to 1 mm.

In further embodiments of the present application, the microfluidic system can have a channel width ranging from about 100 μm to 10 mm, and a channel length ranging from about 1000 μm to about 100 mm. The depth or height of the channel can range from about 20 μm to 1000 μm. The distance between outside edge of corral outer diameter wall and inner edge of channel wall can range from 20 μm to 10 mm.

The microfluidic system can be linear as represented in FIG. 1C, or it can be branched with one or more outlets at the end of each branch.

In another embodiment, the corrals are configured and arranged within the passage to form a rheotactic region proximate to the partially open side of each of the one or more corrals.

As used herein, the term "rheotactic" and "rheotaxis" refer to the ability of an organism to turn and face an oncoming current in a region of fluid flow.

As used herein, "rheotactic region" refers to the region in which the flow of a fluid through that region can create rheotaxis in motile cells. A "motile cell" is a cell that is able to move spontaneously and actively (e.g., by movement of flagella and/or cilia). Exemplary motile cells include sperm cells, such as mammalian sperm cells, and certain bacteria, such as *Bacillus subtilis*.

The ability of sperm to swim upstream (Zhang et al., "Human Sperm Rheotaxis: A Passive Physical Process," *Sci Rep* 6:23553 (2016), which is hereby incorporated by reference in its entirety) enables these microswimmers to travel distances over 10,000-times longer than their head-to tail length in order to fertilize an oocyte. This important attribute of sperm results from the hydrodynamic interactions of sperm with walls and the front-back asymmetry of their shape (Tung et al., "Emergence of Upstream Swimming via a Hydrodynamic Transition," *Phys Rev Lett* 114(10):108102 (2015), which is hereby incorporated by reference in its entirety). In the absence of an external fluid flow, sperm locomotion is roughly circular in both right and left-handed modes (Miki et al., "Rheotaxis Guides Mammalian Sperm," *Curr Biol* 23(6):443-452 (2013), which is hereby incorporated by reference in its entirety). However, in the presence of an external fluid flow, different torques exist on the head and tail of the sperm, due to the difference in resistive forces applied to each. This generates a rotation, causing sperm to orient themselves in the opposite direction of the fluid influx. This mechanism is utilized by sperm as a navigational system to track and fertilize the oocytes (Kantsler et al., "Rheotaxis Facilitates Upstream Navigation of Mammalian Sperm Cells," *Elife* 3:e02403 (2014), which is hereby incorporated by reference in its entirety). The upstream swimming, rheotactic behavior of sperm is observed for a discrete shear rate of the surrounding fluid (Miki et al., "Rheotaxis Guides Mammalian Sperm," *Curr Biol* 23(6):443-452 (2013); Tung et al., "Microgrooves and Fluid Flows Provide Preferential Passageways for Sperm Over Pathogen Tritrichomonas Foetus," *Proc Natl Acad Sci* 112(17):5431-5436 (2015); Zhang et al., "Human Sperm Rheotaxis: A Passive Physical Process," *Sci Rep* 6:23553 (2016), which are hereby incorporated by reference in their entirety). A minimum threshold shear rate for sperm orientation is required, while shear rates above the maximum threshold will prevail over the force produced by the sperm flagellum (Bukatin et al., "Bimodal Rheotactic Behavior Reflects Flagellar Beat Asymmetry in Human Sperm Cells," *Proc Natl Acad Sci* 112(52):15904-15909 (2015), which is hereby incorporated by reference in its entirety). There are some reports suggesting that velocities in the range of 27-110 µm/s for bovines and 22-102 µm/s for humans can lead to sperm rheotaxis (Miki et al., "Rheotaxis Guides Mammalian Sperm," *Curr Biol* 23(6):443-452 (2013); Tung et al., "Emergence of Upstream Swimming via a Hydrodynamic Transition," *Phys Rev Lett* 114(10):108102 (2015); Tung et al., "Microgrooves and Fluid Flows Provide Preferential Passageways for Sperm Over Pathogen Tritrichomonas Foetus," *Proc Natl Acad Sci* 112(17):5431-5436 (2015), which are hereby incorporated by reference in their entirety). For this reason, the microfluidic investigations began at these two velocity ranges, as they are consistent with the typical physical and biological properties experienced by the sperm samples.

Unlike the forces produced by the medium flow, sperm progressive motility that results from the flagellum's propulsive force (Tulsiani, D. ed, *Introduction to Mammalian Reproduction*, Springer Science & Business Media (2012), which is hereby incorporated by reference in its entirety) cannot contribute to its upstream orientation. Once a sperm swims in a shear flow, its head will be closer to the top surface of the corral system where it is barely influenced by the flow, while its tail experiences a greater force, as shown in FIG. 1B. Based on the resistive force theory, the torque resulting from this situation rotates the sperm in the top view plane around its pivot (head) as depicted in FIG. 1C. The angular velocity of this rotation ($\Omega$) can be described by Eq. 1 (Tung et al., "Emergence of Upstream Swimming via a Hydrodynamic Transition," *Phys Rev Lett* 114(10):108102 (2015), which is hereby incorporated b reference in its entirety), $$\Omega = \frac{d\theta}{dt} = -A\gamma \sin \theta \quad [1]$$

in which $\gamma$ is the shear rate of the sperm medium near the wall (viable sperm mostly swim in the vicinity of the wall) and A is a constant related to the geometry of the microswimmer (Tung et al., "Emergence of Upstream Swimming via a Hydrodynamic Transition," *Phys Rev Lett* 114(10): 108102 (2015); Tung et al., "Cooperative Roles of Biological Flow and Surface Topography in Guiding Sperm Migration Revealed by a Microfluidic Model," *Lab Chip* 14(7): 1348-1356 (2014), which are hereby incorporated by reference in their entirety). This rotation is temporary and once the sperm finds its consistent orientation ($\theta=0$), it starts swimming upstream with the propulsive force provided by the flagellum (Zottd et al., "Nonlinear Dynamics of a Microswimmer in Poiseuille Flow," *Phys Rev Lett* 108(21): 218104 (2012), which is hereby incorporated by reference in its entirety).

Additionally, the microfluidic system of the present application can also have a pump positioned to move fluids within the passage from the first end of the housing to the second end of the housing. One common injection system applicable for use in the present application is a syringe pump (e.g., Chemyx Fusion 200). The pumps can be used to control the flow rate of the sperm medium, although any kind of injection systems including micro pumps, syringe pumps, and surface acoustic waves may be used. Different injection rates can be utilized to fine tune the selectivity of the motile cells that enter the confinement region.

Furthermore, the corrals can include one or more retainers (or retentors) to maintain motile sperm or bacteria within the confinement region. Exemplary retentors can be seen in FIG. 4A.

The system may also include a heating unit for maintaining the system at a desired temperature, such as between 25 and 37 degrees Celsius. In addition, the system may have an incubator where physiological conditions are mimicked. In particular, physiological conditions such as oxygenation, carbon dioxide and/or nitrogen concentrations can be controlled. Other factors such as e.g. humidity may also be controlled. The system may also include a separate oxygenator.

The fabrication process of the microfluidic system of the present application can be accomplished using wet and dry etching, thermoforming, polymer ablation and polymer casting. In one embodiment, conventional soft lithography is used to create the microfluidic system, (Xia et al., "Soft Lithography," *Annu Rev Mater Sci* 28(1):153-184 (1998), which is hereby incorporated by reference in its entirety).

Further examples of fabrication processes useful for the creation of microfluidic systems are disclosed in U.S. Pat. Nos. 6,802,489; 6,929,030; 7,918,244; 9,364,831; and 8,691,010, which are hereby incorporated by reference in their entirety.

Microfluidic systems are traditionally fabricated by the wet or dry etching of silicon or silicon dioxide substrates. Because transparency and low channel aspect ratios are indispensable in certain situations, however, a procedure in which plasma etched silicon wafers are used as templates for the creation of replicas cast in poly(dimethylsiloxane) (PDMS), a clear elastomeric material, has been adopted. The methodology used to create such elastomeric microfluidic networks is further described; however, the fabrication of the microfluidic networks of the present application is not limited to PDMS substrates. Glass, silicon, and other materials that microfluidic systems are commonly manufactured from may be used instead of PDMS.

Photolithography describes the general process of using radiation to produce a desired pattern in a photosensitive material. Templates of the microfluidic system are created lithographically with ultraviolet (UV) light by transposing the pattern of a chrome mask upon UV sensitive negative photoresist. The patterns are subsequently developed in an appropriate solution, leaving only the relief of the desired pattern, which may be used directly as a PDMS master or etched to produce a permanent master. If used as the structural material to directly create PDMS replicas, photoresist films may be readily prepared with thickness from 100 nm to 100 µm, thus providing a wide range of accessible aspect ratios.

Soft lithography describes the generic replication of a mold in PDMS. PDMS replicas are created using a commercially available two-component kit, such as Sylgard 184 Kit, Dow Corning. A mixture of elastomer and curing agent are poured over the silicon master and cured under vacuum to degas the elastomer solution. PDMS makes an ideal candidate for microfluidic system production, because it can be cured rather rapidly. Patterns are faithfully reproduced and the process can be conducted in a non-clean room environment. Furthermore, the design and fabrication of microfluidic networks becomes increasingly flexible as masters may be fabricated with more complex designs and lithography need not solely be relied upon.

Cured PDMS replicas are peeled from the master, leaving a clean, reusable template. The replica is finally placed in conformal contact with either a glass slide or PDMS flat forming a tight, reversible seal and enclosing channels capable of conveying fluids. PDMS is natively hydrophobic but can be easily modified to create a hydrophilic surface through brief exposure to an oxygen plasma. Replica films >50 µm may also be created by spin coating PDMS onto a silicon master. Such films may be used as shadow masks for the deposition of metal features, such as electrodes, onto other replicas or multiple films may be stacked to create three-dimensional microfluidic networks.

The microfluidic systems may also be created by using reactive ion etching (RIE), commonly referred to as plasma etching. RIE is employed to either etch channels into glass or silicon or to create permanent masters for PDMS replication in silicon wafers. RIE is favored over wet etching techniques in many applications, because it provides the possibility of forming channels of variable aspect ratio as low as one, with relatively straight walls and rapid etch rates. Due to the isotropic nature of wet etching with hydrofluoric acid (HF), the maximum possible aspect ratio (channel height divided by width) is 0.5. Anisotropic wet etching with potassium hydroxide (KOH) will selectively etch along silicon's (1,1,1) crystal face producing features with vertical walls; however, the etch rate is slow relative to those available vie RIE.

Metal deposition may also be used for the creation of the microfluidic systems of the present application. Electrodes and control circuitry created from thin films of aluminum, copper, or gold may be lithographically templated upon microfluidic chip substrates by two principle methods: evaporation and liftoff or evaporation and "peel-off". Evaporation and liftoff is a conventional technique appropriate for the deposition of metals upon rigid substrates such as silicon or glass. The desired pattern is photolithographically generated in positive photoresist before metal is evaporated and deposited over the entire substrate. Finally, the metal-coated photoresist is stripped in an appropriate solvent, such as acetone, leaving only the original pattern. Evaporation and liftoff is an efficient means of creating intricate circuitry upon rigid microfluidic chip faces; however, it is inappropriate for flexible chips cast in PDMS. Therefore, a technique referred to as shadow mask "peel-off" can be employed to replace photoresist lift off. Instead of patterns created in photoresist, a negative relief mask is cast by spin coating PDMS onto etched silicon wafers to depths less than that of the features on the master. This shadow mask is then peeled from the master and placed upon the PDMS microfluidic chip replica and metal is deposited over the entire system. When the shadow mask is peeled from the PDMS chip, the desired circuitry pattern remains.

A further process suitable for the creation of the microfluidic system of the present application is rapid prototyping. A combination of techniques discussed above, photolithography and soft lithography, have previously been utilized in conjunction with the creation of high-resolution shadow masks as an experimental fabrication method in which proposed designs may be conceived, tested, and manufactured within the span of a single day. This process, which is limited to fairly large microstructures (>15 µm) by the resolution of available printers or image setting techniques, has been dubbed "rapid prototyping", and allows for quick inexpensive testing of design options. In the process, masks are drafted using commercial software, such as Macromedia Freehand, Quark Express, or Adobe Illustrator, and printed on a transparency or image set on photographic film, which is then used as a shadow mask to replicate the design in negative photoresist. As etching of the design into the silicon is not required to make a single-use master, a PDMS replica is cast directly upon the photoresist, thus generating a "rapid prototype" microfluidic network.

The above operations may be combined in a variety of ways in order to fabricate the microfluidic systems of the present application.

The microfluidic system of the present application can also include an imaging system configured to capture a plurality of images of at least a portion of the microfluidic system. The imaging system includes a light source configured to illuminate the at least a portion of the microfluidic channel; and a detector configured to detect an image, e.g., a shadow image, of the motile cells in the illuminated portion of the microfluidic channel.

The integration of the microfluidic system with an imaging system enables a population of sperm or bacteria, or an individual sperm or bacterium in the microfluidic channel to be tracked and analyzed. In some embodiments, the imaging system is a lensless imaging system that achieves automatic and wide field-of-view imaging of the channel or corral of the microfluidic system. In other embodiments, the imaging system is a light microscope with, e.g., a 10× objective lens. The imaging system includes a light source, such as a light-emitting diode (LED) or other light source. The light source illuminates one or more corrals of the microfluidic system. An image sensor can be placed on the opposite side of the microfluidic system from the light source. When light is incident on a corral, sperm in the illuminated corral diffract and transmit light. Shadows generated by diffraction of the light by the sperm are imaged by the image sensor, generating shadow images of the population of sperm in the corrals. The image sensor may be any appropriate sensor, such as a charge-coupled device (CCD) sensor or a complementary metal-oxide-semiconductor (CMOS) chip based sensor.

The lensless imaging system generates shadow images of sperm in the channels quickly (e.g., in about one second) and with a wide field of view (FOV). For instance, the FOV of the imaging system may be a few millimeters by a few millimeters (e.g., 4 mm×5.3 mm) up to as large as a few centimeters by a few centimeters (e.g., 3.725 cm×2.570 cm), or another size appropriate to image a portion of or the entirety of one or more corrals of the microfluidic system.

In some cases, hundreds of thousands of individual sperm or bacteria may be encompassed by the FOV of the imaging system. Furthermore, because of the wide FOV of the imaging system, each individual sperm/bacterium stays within the FOV of the imaging system for a relatively long period of time. Thus, sperm or bacteria motion and activity can be tracked and analyzed for a large number of cells, collectively or individually, over a long period of time, enabling accurate statistics to be acquired. In some embodiments, the imaging system is designed to image sperm within the FOV with sufficient contrast and signal-to-noise ratio to be detected or counted individually, which may in some cases result in a sacrifice in spatial resolution.

The images are processed manually and/or automatically using image analysis software to count, identify, track, and analyze the activity of individual cell or populations of motile cells (e.g., motile sperm) in the imaged corrals. For instance, to analyze images acquired for sperm or bacteria distribution in a particular corral, automated counting and identification of the sperm in each image is performed. The count results are compared to diffraction theory, which includes the distance between the active region of the image sensor (e.g., the active surface of a CCD sensor) and the location of the imaged microscopic object (e.g., the sperm cell) as critical parameters. To quantitatively investigate the effect of cell shadow diameter on the detected signal strength, the captured diffraction signatures of the sperm cells are fitted to a model.

A second aspect of the present application relates to a method for separation of motile sperm from immotile sperm or motile bacteria from immotile bacteria. The method includes providing the microfluidic system of the present application, providing a sperm-containing sample or a bacteria-containing sample, and passing the sperm-containing sample or the bacteria-containing sample through the inlet, through the passage, and through the outlet of the microfluidic system. The motile sperm or motile bacteria are retained within the one or more corrals, while immotile sperm or immotile bacteria are discharged through the outlet.

In the use of microfluidic system 2 (FIG. 1A) for the separation of motile sperm or motile bacteria, a sample is first prepared by diluting the sample containing sperm or bacteria with a chosen buffer, such as Tyrode's albumin lactate pyruvate (TALP) medium. The sample is then loaded into microfluidic system 2 through inlet 12 located on first end 6. A pump, such as a syringe pump may be used to move a biocompatible medium/buffer from inlet 12 to outlet 14, located on second end 8, via passage 10. The flow of the medium/sample should be adjusted to acquire the desired rheotaxis parameters. This can be accomplished by adjusting the flow rate of the pump. During the flow of the sample through passage 10 to outlet 14 the motile sperm or bacterial will enter corrals 16. The sperm or bacterial sample can then be further washed by flushing buffer through inlet 12 to outlet 14 via passage 10. The sperm or bacteria in corrals 16 can be recovered by pipette or injection of the washing media with high flow rates between 5-20 mL/h.

In one embodiment of the present application, the sample includes sperm. In a further embodiment of the present application, the sample includes bacteria. The samples may also contain buffers or other diluents to control the viscosity, pH, ionic strength, and concentration of the sample. Some such materials include phosphate buffered saline (PBS), HEPES (4-(2-hydroxyethyl)-1-piperazineethanesulfonic acid)-buffered saline (HBS), Tyrode's albumin lactate pyruvate (TALP) medium, HEPES buffered human tubal fluid, Tris buffer, ethylenediaminetetraacetic acid (EDTA), physiological saline, buffered saline, nutrient broths, and the like.

The sample may be gently mixed with a medical grade coloring agent, which does not affect fertility and is biocompatible. The coloring agent may e.g. be present within the first side of the microfluidic system prior to loading of the sample and hence is mixed with the sample during loading. Alternatively, the sample may be gently mixed with a low-viscosity buffer which includes a coloring agent prior to loading of the sample into the inlet of the microfluidic system. The coloring agent may e.g. comprise colloid particles or a fluorescent component. The efficacy and functionality of the method may hence be assessed.

A further embodiment of the present application includes recovering motile sperm or motile bacteria from the one or more corrals. Additionally, the sample may be washed prior to recovering motile sperm or motile bacteria. The recovered motile sperm can be utilized in conjunction with an assisted reproductive technology (ART). Some ARTs include intrauterine insemination, in vitro fertilization, and intracytoplasmic sperm injection. U.S. Pat. Nos. 9,499,778; 9,984,278; 7,846,957; and 9,663,755, which were hereby incorporated by reference, disclose various methods of ART.

There are currently a wide variety of artificial insemination methods, such as intracervical, intrauterine (IUI), intratubular and direct intraperitoneal (DIPI) insemination, gamete intrafallopian transfer (GIFT), in vitro fertilization and embryo transfer (IVFET), zygote intrafallopian transfer (such as ZIFT, PROST and TET), peritoneal oocyte and sperm transfer (POST), among others. Regardless of the process; high motile sperm are always preferred. As an example, the Intrauterine Insemination (IUI) and in vitro fertilization (IVF) methods attempt to mimic the reproductive process by placing sperm and eggs together in an environment conducive to fertilization, either in the womb or outside the womb. The fertilization process requires the sperm to actively invade the egg and commence fertilization. Motile sperm are much more likely to penetrate the egg.

Current IVF technology can involve up to eight steps: 1) sperm purification; 2) oocyte capture and isolation; 3) oocyte stripping; 4) intra cytoplasmic sperm injection (ICSI); 5) embryo incubation; 6) embryo & oocyte freezing; 7) embryo & oocyte thawing; and 8) zona hatching and embryo transfer. Purification of sperm from semen, washing away cellular debris, and reconcentration of sperm is an essential requirement for many fertility procedures, including preparation of sperm for intrauterine insemination and for IVF. Purified sperm are used primarily for intrauterine insemination or as the initial preparation for IVF or ICSI.

Another embodiment of the present application includes controlling the flow of the sample through the housing to selectively retain the sperm or the bacteria. The flow of sample through the housing can range from about 0.5 mL/hr to 500 mL/hr.

Furthermore, according to the method of the present application, the microfluidic system may be sterilized, flushed, and/or calibrated before the loading of the sample into the system. This may occur e.g. by a physician, medical trained professional, user, or may have been performed during production, i.e. providing a sterile medical device in e.g. blister packaging or wrapping. Sterilization, flushing, and/or calibration may occur with e.g. ethanol, sterile and/or distilled water, and buffers, respectively.

On the basis of the rheotactic behavior of sperm, an exemplary microfluidic channel was designed featuring seven interior corrals. The width of the channel, its depth, and the outer and inner radii of the corrals are 500 µm, 30 µm, 150 µm, and 100 µm, respectively (FIG. 1A). The rationale behind this design is to create rheotaxis zones in front of each corral using appropriate sperm medium injection rates, thus enabling motile sperm who pass through these regions to reorient themselves and begin swimming towards the opposite direction of the flow until they enter the interior of the corral structure and become trapped. In this manner, healthy, motile sperm can be separated from the rest of the sample, which includes dead, abnormal (motility lower than the minimum cutoff), and misproportioned microswimmers (in which abnormal morphology affects motility).

The velocity field of the sperm medium in the rheotaxis zone should be gentle enough for viable sperm to swim upstream (Miki et al., "Rheotaxis Guides Mammalian Sperm," Curr Biol 23(6):443-452 (2013), which is hereby incorporated by reference in its entirety) as compared to the surrounding velocity in the channel, in which they cannot overcome the flow. Since the corral is an obstacle in the middle of the microfluidic channel, the velocity field of the sperm medium in front of it will be lower than above or below this feature. Thus, using the corral as a barrier, it is possible to create an area in front of this structure in which the velocity field is gentler than in any other region throughout the channel. As illustrated in FIG. 1A, dead sperm (darker sperm) move along the fluid streamlines, but normal and viable sperm (lighter sperm) can swim upstream in front of the corral and eventually enter it, becoming trapped. While some of the motile and live sperm do not enter the rheotaxis zone and consequently cannot enter the corral, all the sperm that do enter this zone, and are motile enough to swim upstream, will enter the corral.

To produce a gentle flow in front of the corrals that encourages the upstream swimming behavior of motile sperm (thus trapping them inside the structures), FEM simulations were conducted in order to estimate an appropriate range for the sperm medium injection flow rate. Momentum and mass conservation equations were solved using no-slip boundary conditions at the walls, enabling us to extract the velocity field across the microfluidic layout. The velocity field is expressed in Y-Z cut planes at four different positions, as can be seen in FIG. 5A, and the contour levels corresponding to each of these positions is demonstrated in FIG. 5B. It was also demonstrated the velocity field in an X-Y cut plane featuring a depth as half as large as the depth of the channel in FIG. 5C, in which the direction of the velocity field at each calculated point is depicted using arrows. Within the corral, the velocity field is zero and the medium is shown to be quiescent. Since transportation of dead sperm relies on drag force, the absence of streamlines entering the corral supports the previous assertion that no dead sperm can enter the structure.

The rheotactic behavior of the sperm in the vicinity of the microfluidic channel's top surface is correlated to the shear rate of the fluid in that region in the Z direction. Therefore, the shear rate distribution on the top surface was calculated, which is shown in FIG. 5D for an injection rate of 1.2 mL/h. In this figure, the light color corresponds to a shear rate of $\gamma=8.21$ s$^{-1}$ while the minimum shear rate ($\gamma=0$) is shown in black. Since the evolution of sperm orientation is determined by the shear rate in proximity of the top surface, this shear profile throughout the structure and in the vicinity of its top surface was required to simulate sperm movement in front of the corral. Moreover, to experimentally determine the minimum shear rate required for sperm to undergo rheotaxis, the shear rate in the rheotaxis zone must be known.

To provide a more vivid understanding of the fluid flow in front of the corral, the velocity field for different flow rates (0.6-1.8 mL/h with steps of 0.12 mL/h) along the X axis were reported, where X is shown in FIG. 5D. According to the simulations, the velocity field of the sperm medium is zero near the corral wall. As X increases, the velocity field of the medium also increases, until it finally reaches a constant value between 110-135 µm/s (depending on the injection rate) at approximately 300 µm from the corral (FIG. 5E).

If the shear rate in the rheotaxis zone is above a threshold value, then all the motile sperm will be able to orient themselves in an upstream direction, with the angular velocity varying depending on the shear rate at the reorientation point. However, reorientation cannot guarantee the entrance of sperm into the corral. Sperm must be motile enough to overcome the fluid flow. Therefore, the fraction of the sperm that are motile enough to move towards the corral depends on the velocity field within the rheotaxis zone. Higher flow rates lead to a smaller fraction, whereas lower flow rates increase the portion. Therefore, the resolution of the motility-based sperm selection in the corral is proportional to the velocity field within the rheotaxis zone.

Figure 5G:
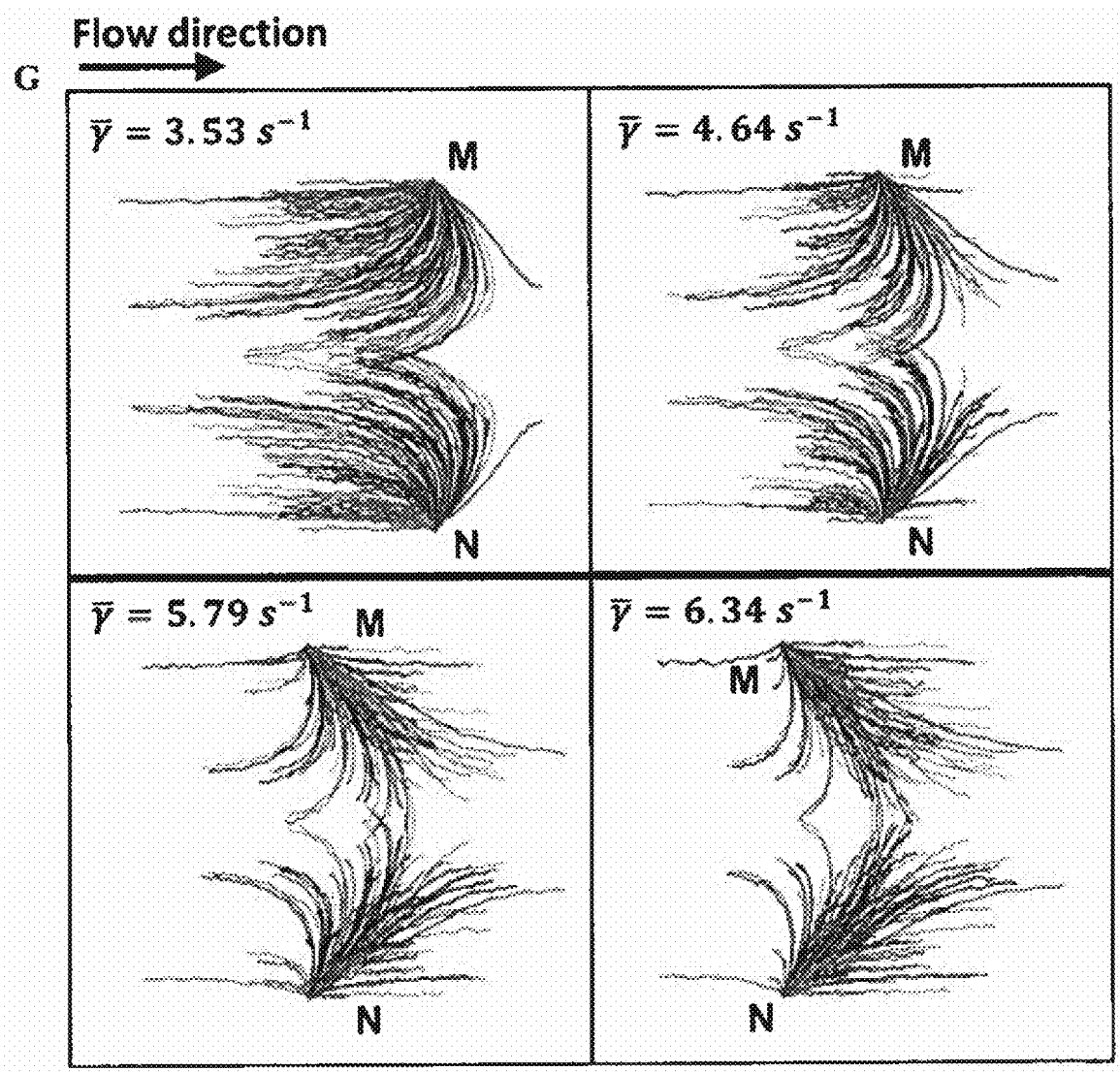

To model and calculate the fraction of sperm that can enter the corral as a function of flow rate, the equations of the sperm motion within the rheotaxis zone (FIG. 5F) were solved. It was assumed that sperm propulsive velocity does not change over time and its direction evolves as equation 1 describes. It was also assumed that sperm has a lateral head movement that can be modeled as white Gaussian noise $\xi(t)$ using $\langle \xi(t)\xi(t') \rangle = \delta(t-t')$. The equations of the motion for 400 sperm were solved, with a normal velocity distribution and a uniform initial direction, entering the rheotaxis zone from the top-left (point M) and the bottom-left (point N) corners with the rate of $Q_{in}$ (i.e., the number of sperm entering the rheotaxis zone per second) (FIG. 5F). As the flow/shear rate increases the number of sperm moving upstream decreases, as it can be seen in FIG. 5G. Consequently, it was expected that the shape of the sperm velocity distribution inside the corral will be narrower as the flow rate increases.

EXAMPLES

The following Examples are presented to illustrate various aspects of the present application, but are not intended to limit the scope of the claimed invention.

Materials and Methods

Fabrication of Microfluidic System

The master mold of the chip was made on a 30 µm thick SU-8 photoresist using a standard photolithographic technique. Then a polydimethylsiloxane (PDMS) solution with a weight ratio of 10:1 (PDMS:thickener) was mixed and poured on the master mold and after the mixture was degassed, PDMS was cured at 70° C. for 1 hour in oven and then the replicated PDMS channel layer was peeled off from the master mold and bonded to a clean glass substrate using plasma bonding system. Hole(s) for the inlet(s) and for the outlet(s) were punched on the micromixer. Two tubes were connected to the inlet and outlet holes of the chip. The adhesion of glass tubes to the inlets and the outlet in different flow rates was tested to make sure that there is no leakage in the connections. The system was sealed. Syringe pumps (Chemyx Fusion 200) were used to control the flow rate of the sperm medium at different injection rates of 0.6, 1.2, and 1.8 mL/h.

Human and Bovine Sperm Medium

A human semen sample was generously provided by Weill Cornell Medical School. This fresh semen sample was first diluted with Tyrode's albumin lactate pyruvate (TALP) medium (Tung et al., "Microgrooves and Fluid Flows Provide Preferential Passageways for Sperm Over Pathogen Tritrichomonas Foetus," *Proc Natl Acad Sci* 112(17):5431-5436 (2015), which is hereby incorporated by reference in its entirety) and kept at a constant temperature of 37° C. for the duration of the experiment. Cryopreserved bovine samples from four different bulls were generously donated by Genex Cooperative (Ithaca, NY). Semen from two of the bovines was frozen in a milk-based extender and semen from the other two bulls was frozen in an egg-yolk based extender in 250 µL straws at a concentration of 100 million sperm/mL. The frozen straws were thawed in a 37° C. water bath and diluted 1:1 with TALP medium prior to use. After dilution, the dynamic viscosity of the human and bovine sperm samples was 3.42 and 2.11 mPa-s, respectively. Using the relation established for the Re number:

$$Re = \frac{\rho U L}{\mu}$$

it was determined that the Re numbers for the three different flow rates are ~1.05, 2.10, and 3.15×10⁻², respectively. In the experiments, 10 replicates of the bovine samples and 3 replicates of the human sample were used.

Image and Video Acquisition

Images and videos were acquired at 25 frames per second using phase contrast microscopy with a 10× objective and a digital Neo CMOS camera. During the experiments, the microfluidic chip was kept on a heated microscope stage (Carl Zeiss, at 37° C.). The average path velocity of the sperm was determined using ImageJ (Version 1.51j8) and MATLAB (Version R2017a) software by measuring the average distance between the center of the sperm head in each frame divided by the time elapsed.

Simulation Software

To simulate the sperm motion within the rheotaxis zone, the velocity field and the shear rate inside the zone extracted from the FEM simulations. Then, using MATLAB R2017a, the equations of the sperm motion was solved by assuming that sperm have a normal distribution for velocity and a uniform distribution for initial direction. The sperm direction evolved by Eq. 1, and its movement in vicinity of the top surface, assumed to be affected just by its propulsion and velocity field of the medium.

The layout of the microfluidic device was imported into COMSOL MULTIPHYSICS (Version 5.2) simulation software. Using the laminar fluid module in stationary mode, the Navier-Stokes (Eq. 2) and conservation of mass (Eq. 3) equations with no-slip boundary condition at the walls were solved. The simulations were performed for eleven input flow rates between 10 µL/min and 30 µL/min at 2 µL/min steps.

$$\rho(v \cdot \nabla v) = -\nabla p + \nabla \cdot \mu (\nabla v + (\nabla v)^T) \quad [2]$$

$$\nabla \cdot v = 0 \quad [3]$$

Where v denotes velocity field, ρ is the density of the sperm medium, p is pressure, and µ is the dynamic viscosity.

Example 1—Motile Sperm Separation

In addition to simulations, the motion of sperm in the fabricated microfluidic device featuring 7 corral structures was also studied. The dynamic of trapped sperm inside an individual corral for both bovine and human samples is shown at different times in FIG. 6. According to these images, the trapped sperm are motile and viable, and their motilities are seemingly normal (~65-89 µm/s for bovine and 58-81 µm/s for human). All the isolated sperm have a regular tail beating pattern and normal lateral head movement and show a strong tendency to swim in proximity of the interior walls of the corral (see also FIG. 7 and the trajectories of the sperm). In FIG. 6A, at t=1 s, a bovine sperm enters the corral and at t=10 s, the number of isolated bovine sperm has increased to 10 (FIG. 6B). In addition to the increasing number of isolated sperm, the dynamic of sperm inside the corral includes their hydrodynamic interactions with the interior walls. In fact, once the sperm encounter the interior walls, they start rotating to swim along the walls, and eventually, most of the sperm accumulate near the interior wall, as can be seen in FIG. 6B. An increase in the number of isolated sperm and accumulation near the interior wall is also observed for human sperm (FIGS. 6C and 6D). Since the velocity field inside the corral is negligible, this observation is not correlated to the velocity field of the sperm medium outside the corral.

Once the sperm enter the corral, they move with their own propulsion force and their motility is not affected by the velocity field of the medium. Due to hydrodynamic interactions between sperm and the interior wall of the corral, they tend to move parallel to the interior boundary and finally exit the corral. This short residence time of the sperm within the corral, can be used for clinical studies including the investigation of sperm response to different drugs.

To validate the hypothesis that rheotactic behavior can guide sperm towards the corrals, video of sperm movement inside the microfluidic device was recorded. As shown in FIGS. 7A and 7B, bovine and human sperm, respectively, were tracked swimming upstream and entering the corral. The black ovals label sperm that are undergoing rheotaxis, whereas the white ovals indicate sperm that have already been isolated within the corral and have stopped moving upstream, returning to their original flow-free swimming pattern. These figures highlight only a small portion of the total number of sperm (~150) swimming upstream to convey the separation mechanism.

The trajectories of both bovine and human sperm were extracted and demonstrate them in FIGS. 7C and D, respectively. The black circles represent the starting point of each trajectory. Based on these patterns, one can see that the sperm begin to swim upstream once they enter the rheotaxis zone behind the corral. It takes less than 2 s for the sperm to transition their swimming direction towards the opposite direction of the flow. Based on the earlier theoretical model provided, this orientation of the sperm cell is anticipated, and it is already known that the time of the rotation is correlated to the shear rate around the sperm close to the wall, as seen in Eq. 1. This change of direction is discernible in the trajectories of some sperm in both FIGS. 7C and 7D, as indicated with arrows. As illustrated in FIGS. 7C and 7D, most of these trajectories finish near the interior wall of the corral.

In addition, to quantitatively assess the role of rheotaxis in increasing the isolation efficiency of motile sperm inside the corral device, and to experimentally confirm the theoretical model, the distribution of movement of the sperm in front of the corral as a function of flow rate was investigated. The distribution of the sperms' movement status for both human and bovine samples is presented in FIGS. 8-10, which demonstrated that the percentage of upstream-reoriented sperm within the rheotaxis zone was ~35-50%. This percentage shows that providing the rheotaxis zone in front of the corral increased the number of isolated sperm.

In FIG. 8, the trajectories of the human sperm in front of the corral have been extracted for both upstream-reoriented (FIG. 8A) and upstream-oriented (FIG. 8B) swimmers when the flow rate is 0.6 mL/h. The distribution of the sperm movement status for human and bovine samples is depicted in FIG. 8C. Likewise, the distribution of the sperm movement status when the flow rate is 1.2 mL/h and 1.8 mL/h is depicted in FIG. 9 and FIG. 10, respectively. Sperm orientation can be either upstream or downstream. However, since the velocity field of the sperm medium is not zero outside of the corral, having upstream or downstream orientation is inadequate to determine the movement direction of the sperm. Therefore, the sperm were categorized into four different groups: (1) upstream-reoriented sperm moving upstream; (2) upstream-oriented sperm moving upstream; (3) upstream-oriented and reoriented sperm moving downstream; and (4) downstream-oriented sperm moving downstream. The term "upstream-reoriented sperm" is used for sperm with directions not originally orientated upstream but in the rheotaxis zone, in which they underwent rheotaxis and reoriented toward the upstream direction. Moreover, the term "upstream-oriented sperm" is used for sperm that originally moved in the upstream direction. These distributions, and the portion of sperm displaying rheotactic behavior but cannot enter the corral as a function of flow rate demonstrates the tunability of the device. Moreover, these experimental values corroborate the proposed theoretical movement of sperm motion within the rheotaxis zone.

As experimentally determined, each corral can capture a maximum of 2% of the injected sample, and as there are 7 corrals in the device that was used, this amounts to a total capture of 14% of the injected sperm. This means the number of captured sperm by each corral is negligible in comparison with the total sperm number, and therefore the captured sperm by the first corral will not affect the sperm movement distribution in the rheotaxis zone of the second corral dramatically, and so on. Therefore, the distribution of sperm movement extracted for sperm within the rheotaxis zone is the same for all corrals.

In order to statistically confirm the hypothesis, the effects of the experimental conditions on the distribution of the movement status variable including sperm type (i.e., human/bovine, HB), shear rate (SR), and movement status (MS) was studied. An analysis of covariance model that includes HB and MS as categorical variables and SR as a numerical variable and the interaction between SR and MS as independent variables was fitted to the experimental data. The overall F-test for the model was significant at the 0.05 level (p-value=0.0001). Furthermore, it was found that HB was not significant (p-value=0.89), which means no significant difference in the distribution between the bovine and human sperm samples was observed. The interaction effect of SR and MS was significant, which means that the effect of SR depends on the level of the MS. The nature of this interaction can be seen in FIGS. 8-10.

To model and calculate the fraction of sperm that can enter the corral as a function of flow rate, the equations of the sperm motion within the rheotaxis zone for 400 sperm with a normal velocity distribution and a uniform initial direction were solved, entering the rheotaxis zone from the top-left (point M) and the bottom-left (point N) corners with the rate of $Q_{in}$ (i.e., the number of sperm entering the rheotaxis zone per second). It was assumed that the total velocity of the sperm is the sum of its own propulsive velocity and the velocity field of the sperm medium. The minimum, maximum, and mean values of the sperm velocity were assumed to be 40, 90, and 65 μm/s, respectively. The velocity field and the shear rate in proximity of the top surface were imported from FEM simulations. It was also assumed that a minimum shear rate for all sperm to undergo rheotaxis exists and all sperm had enough time to reorient themselves. To model the rate of sperm accumulation inside the corral, the portion of sperm in the rheotaxis zone that are motile enough to swim toward the corral was determined. Therefore, assuming that the mean value of the medium velocity within the rheotaxis zone is $v_r$, the rate of sperm that can accumulate inside the corral ($Q_{corral}$) over $Q_{in}$ is described by Eq. 4, $$\frac{Q_{corral}}{Q_{in}} = \int_{v_r}^{v_{max}} U(v)dv \quad [4]$$

in which U(v) is the velocity distribution of the sperm in the rheotaxis zone ($\int_{v_{min}}^{v_{max}} U(v)dv=1$) and $v_{max}$, is the velocity of the sperm with maximum motility. This equation for a normal distribution of N(μ, σ) reduces to Eq. 5, $$\frac{1}{2}\left[\text{erf}\left(\frac{v_{max}-\bar{v}}{\sqrt{2}\sigma}\right) - \text{erf}\left(\frac{v_r-\bar{v}}{\sqrt{2}\sigma}\right)\right] \quad [5]$$

in which $\bar{v}$ and σ are the mean and standard deviation of the sperm velocity distribution. The curve acquired from Eq. 5 is juxtaposed with experimental results and as it is demonstrated in FIG. 10, the experimental results confirms the proposed model.

Figure 11:
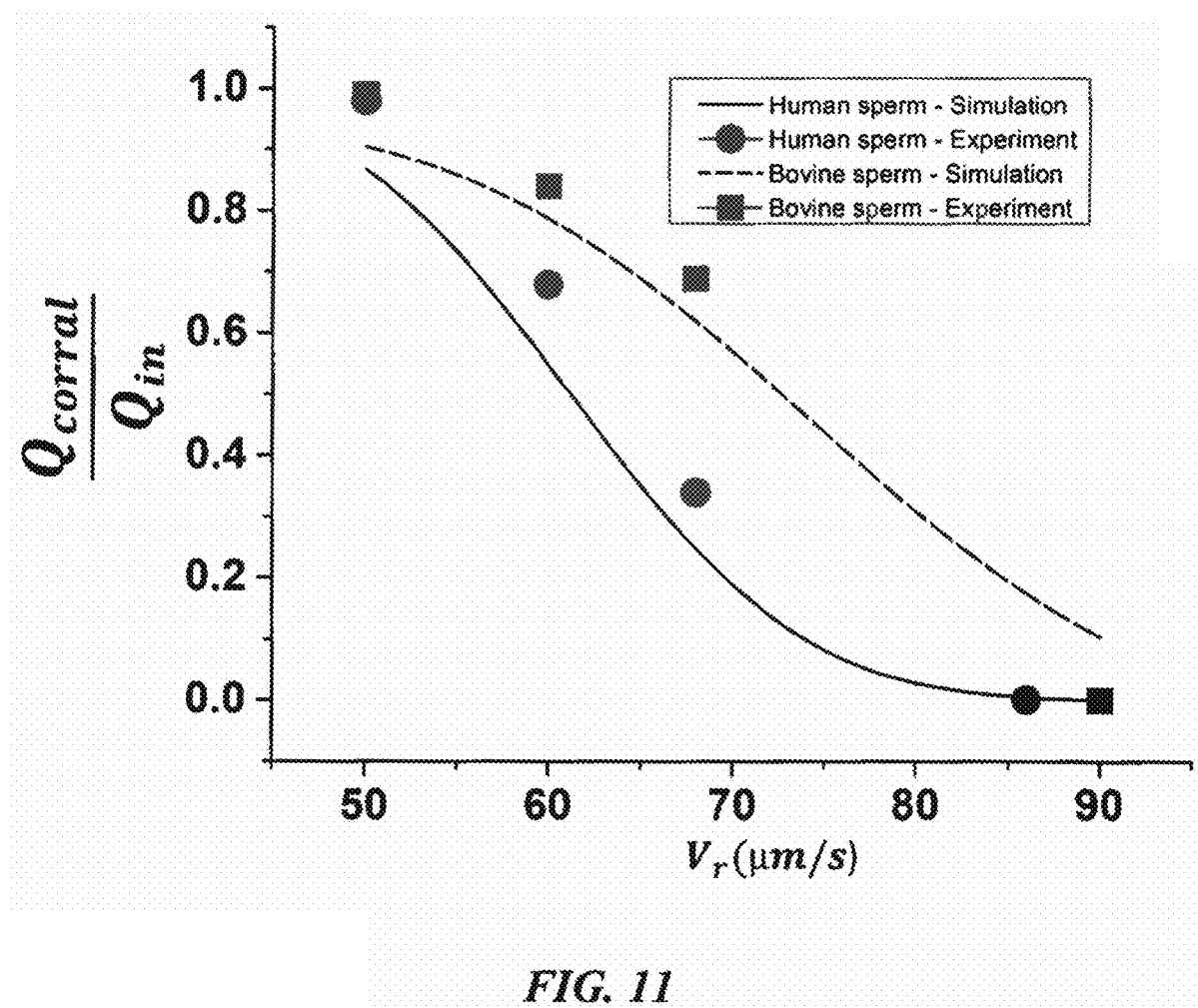
FIG. 11 is a plot of $$\frac{Q_{corral}}{Q_{in}}$$

The experimental results agreed with the corresponding corral tunability in capturing the sperm, predicted by simulation-based results and the values acquired from the experimental data are juxtaposed with the simulation-based results for both human and bovine sperm samples and are demonstrated in FIG. 11.

As the shear/flow rate increased (FIGS. 8-10), the average velocity field inside the rheotaxis zoned also increased, and, therefore, the number of viable sperm with enough motility to enter the corral decreased, as can be seen in FIG. 10. In fact, this was speculated from the model that the fraction of the sperm that entered the rheotaxis zone and were motile enough to move toward the corral is a function of the flow rate. This function, as demonstrated in the model, is an error function (Eq. 2) for a normal distribution of the sperm velocity. The mean velocity for both human and bovine sperm were measured to be 61.23±11.1 and 74.2813.4 μm/s, respectively. The curve obtained from the model based on these two mean values is shown in FIG. 11. To compare the experimental values calculated as $$\frac{Q_{corral}}{Q_{in}}$$

with the simulation-based values, the experimental data for both human and bovine sperm is also depicted in the figure. At a low flow rate ($V_r$~52 μm/s) almost all the sperm entering the rheotaxis zone can move toward the corral. Once the injection rate provides a mean velocity field of ~60 μm/s in the rheotaxis zone, the number of human sperm moving toward the corral drops to 75%, whereas this portion for bovine sperm is roughly 84%. Eventually, in a high flow rate ($V_r$~68 μm/s), the portion falls to 38% for human sperm. Interestingly, 75% of the bovine sperm were still motile enough to move toward the corral at this flow rate. When the injection rate exceeds a maximum threshold ($V_r$~85 μm/s), no sperm can move toward the corral (FIG. 11).

Example 2—Minimum Shear Rate

To determine the minimum shear rate at which sperm can undergo rheotaxis and reorient themselves upstream, the swimming distribution for sperm within the rheotaxis zone for three different flow rates including 0.1, 0.5, and 0.6 mL/h were experimentally extracted (FIG. 12). When the flow rate was 0.1 mL/h ($\bar{\gamma}$=0.61 s$^{-1}$), all the sperm moved in their original direction and no reorientation process was observed, as it is demonstrated in FIG. 12A. Likewise, at a flow rate of 0.5 mL/h ($\bar{\gamma}$=3.011 s$^{-1}$), sperm did not undergo rheotaxis (FIG. 12B). Once the flow rate was 0.6 mL/h ($\bar{\gamma}$=3.43 s$^{-1}$), all motile sperm in the rheotaxis zone stated to reorient toward upstream (FIG. 12C). It was found that the minimum shear rate required for sperm to display rheotactic behavior was $\gamma_{min}$=3.43±0.12 s$^{-1}$.

Example 3—Velocity Distribution

To quantitatively report the motility of the captured sperm, the velocity distribution of the isolated microswimmers inside the corral was calculated (FIG. 13). To calculate the velocity of a single sperm, the progressive distance covered by the motile sperm was measured. Next, by dividing this distance by the elapsed time, it is possible to obtain the average progressive velocity of each sperm. These velocities were measured inside the corral where the velocity field is zero. As a result, the reported velocity of the sperm is solely due to their own propulsion force. It was observed that the velocity of sperm with maximum abundancy (in terms of the number of isolated sperm) is not associated with the input flow rate (FIG. 13). As long as the injection flow rate (~10-30 μL/min) produces a moderate velocity field in front of the corral, the maximum abundance for the human sperm occurs for those displaying a velocity of 55-65 μm/s. The corresponding velocity range of the most abundant captured bovine sperm was 70-80 μm/s. Overall, most of the sperm in the collected samples are motile and normal in morphological appearance. The robust performance of this device at different injection flow rates suggests the rheotaxis-based separation is successful and consistent under different conditions. The velocity distribution of the isolated sperm remains nearly constant despite user-variability and small variations in the fluid flow rate, which is a common and inevitable noise source in all injection systems.

Furthermore, as established in the velocity distributions of FIG. 13, there is a lower cutoff for the velocity of the isolated sperm. This minimum cutoff is principally related to the injection rate and depends on the type (i.e., the species used) and quality of the semen sample. In FIG. 13, it is demonstrated that the number of sperm with motilities lower than the minimum cutoff (40 μm/s) is zero. These zero values confirm that the entrance of dead sperm and sperm with low motilities is hampered, and hence this device ensures that all isolated sperm are normally motile. This level of isolation efficiency (up to 100%) is desirable for ARTs as an alternative to current sperm separation methods.

Example 4—Tunable Isolation of Sperm Based on Motility

Another characteristic of the microfluidic system of the present application is its motility-based tunability in sperm selection. As described previously, when the flow rate increases, sperm will be selected in a narrower motility range based upon rheotactic behavior and the sperms' ability to overcome the fluid flow, causing the minimum sperm velocity cutoff to increase (FIG. 13). When the injection rate increases, sperm with motilities lower than the new cutoff cannot swim upstream and, consequently, cannot enter the corral, while sperm with high motility are still able. As such, one can use the injection rate to control the motility range of the separated sperm. In the data presented herein, it is demonstrated that one can hinder sperm with motilities lower than 55 μm/s in human samples and lower than 53 μm/s in bovine samples from entering the corral. For both bovine and human sperm, as the flow rate increased, the minimum cutoff in the velocity distribution also increased. These distributions agree with the previous model- and experiment-based results (FIG. 11) and indicates that the velocity field inside the rheotaxis zone can be considered a high pass filter, hampering the entrance of sperm into the corral with motilities lower than a minimum cutoff. This similarity between the cutoff for human and bovine sperm may underlie a similarity between their locomotive structures and strategies.

Example 5—Sperm Retainers and Residence Time in the Corral

Upon entrance to the corral, the sperm begin to move with their own propulsive force since the velocity field of the sperm medium is zero in this area. Once a sperm reaches the interior wall of the corral, because of its hydrodynamic interaction with the structure, it starts to move parallel to the wall, and consequently exits back into the microfluidic channel. The residence time of sperm inside this corral design is 10.2±4.6 s and 12.3±3.4 s for bovine and human sperm, respectively, and can be either increased or decreased by changing the size of the corral. As a result, this type of structure can be used for sperm entrapment for a limited time interval, which is still useful for many applications, such as investigating the response of sperm to drug exposure.

To retain all captured sperm inside the corral, which is imperative for sperm sample preparation and ART applications, sperm retainers were designed inside the corral (FIG. 4A). Sperm retainers enabled the corral to keep all trapped motile sperm inside, as the extracted trajectories in FIG. 4B confirm. Following the interior wall, the sperm eventually encounter the corners provided by the retainers and therefore cannot follow the wall any further, as can be seen in FIGS. 4C and 4D for both bovine and human sperm, respectively. If the sperm could by any chance escape the corner, the interior wall steers it again to the inside of the corral.

The sperm retainer design made the corral system extremely stable. All captured sperm (~150 sperm for a poor bovine sample and ~600 sperm for a normal human sample after 2 minutes sample injection) remained within the corral even after washing the semen sample from the main channel with TALP using a flow rate of 5 mL/h. To retrieve the isolated sperm sample, the chip was washed at a higher flow rate of 5 mL/h also using TALP. This amount of shear/flow rate, which is very low in comparison to human and bovine ejaculation, is also much smaller in comparison with the forces sperm experience in conventional separation methods.

100% of the isolated sperm within the corrals are motile, demonstrating the incredible efficiency of the device as judged by the velocity distribution of the separated sperm sample. However, another measure of the device's efficiency is in terms of the total number of isolated sperm in each corral. The microfluidic system of the present invention was able to isolate 1.94±0.32% (1.56±0.1%), 1.03±0.11% (0.98±0.08), and 0.32±0.07% (0.32±0.04%) of the motile and viable human (bovine) sperm inside each corral at flow rates of 0.6, 1.2, and 1.8 mL/h, respectively (FIGS. 14-16). Although the number of captured sperm is determined by the motile vs. non-motile sperm ratio of the sample, the percentage of the motile sperm that are captured by each corral is solely determined by the injection rate.

Example 6—Device Efficiency

The motile vs. non-motile ratio of the injected semen sample directly governs the number of captured sperm inside the corral. That is, when the sample exhibits no motility (i.e., the motile vs. non-motile ratio=0) the number of captured sperm inside the corral is also zero for both bovine and human samples, as can be seen in FIG. 14A. Once the sample features a non-zero motile vs. non-motile ratio, the viable and motile sperm can become captured by the corral so that the number of captured cells appears to correlate with the ratio, as can be seen in FIG. 14B.

To quantitatively establish a relation between the efficacy of the microfluidic corral system and the motile vs. non-motile ratio, samples with different ratios were tested and then the sperm captured by the corral system for both human and bovine samples at different shear rates after 5 min from injection were counted (FIG. 15). The motile vs. non-motile ratio of the original samples was approximately 1:1 and 1:10 for human and bovine samples, respectively. To prepare a zero sperm motility sample (motile vs non-motile ratio=0), all the sperm were killed intentionally by heating the sample for 5 minutes at 60° C. Later, by mixing the original diluted semen with the zero sperm motility sample, human sperm with 1:3 and 1:7 motile vs. non-motile ratios were prepared. Bovine sperm samples were similarly prepared to produce a sample with a 1:20 motile vs. non-motile ratio.

As was expected, an increase in the motile vs. non-motile ratio of each sample led to a greater number of captured sperm. In addition to the motile vs. non-motile ratio, the number of captured sperm is determined by the mean shear rate in the rheotaxis zone, as is demonstrated in FIG. 15. Therefore, the number of captured sperm inside the corral is a function of both shear/flow rate and the motile vs. non-motile ratio of the injected sample.

Although, the motile vs. non-motile ratio of the sample determines the number of the captured sperm, the number of motile cells that are not able to enter the rheotaxis zone is determined by this ratio as well. For instance, a significant portion of the motile sperm are moving parallel to the sidewalls, as can be seen in FIG. 16A. At high motile vs. non-motile ratios, the number of such sperm that are swimming nearby the sidewalls increases as well as sperm entering the rheotaxis zone. Moreover, depending on the shear rate, the number of reoriented-upstream sperm that cannot swim towards the corral increases with an increase in the motile vs. non-motile ratio of the injected sample (FIG. 16A). Therefore, the device separation efficiency should be reported as the percentage of the motile sperm that are captured.

To assess the device's sperm separation ability, the number of sperm moving towards the corral within the rheotaxis zone was counted and divided by the number of all motile sperm in the frame (FIG. 16A). The results in FIGS. 16B and 16C show that despite the change in the number of captured sperm for samples with different motile vs. non-motile ratios, the efficiency of each corral is approximately constant (i.e., independent of the ratio), though it does appear to depend strongly on the shear rate of the sperm medium. For human sperm, each corral can capture approximately 1.94±0.32%, 1.03±0.11%, and 0.32±0.07% of the motile sperm for shear rates of 3.43 s-1, 4.86 s-1, and 6.27 s-1 respectively. For bovine sperm, these numbers are 1.56 f 0.1%, 0.98±0.08%, and 0.32±0.04% for the same shear rates.

The results of FIGS. 16B and 16C clearly demonstrate that the device efficiency is solely determined by the flow rate of the injected sample, and subsequently the shear rate within the rheotaxis zone. That is, the shear rate rules the movement status of the sperm throughout the channel especially within the rheotaxis zone, and thus directly determines the fraction of the captured sperm inside the corral.

Discussion of Examples 1-6

The viability and motility of sperm in a semen sample is vital for mammalian reproduction. Several centrifugation-based methods are currently used to separate motile sperm from semen samples in order to increase the effectiveness of various ARTs. These conventional methods are time-consuming and labor-intensive and have been reported to be detrimental to the morphology and paternal content of the sperm. In this work, a new microfluidic high-throughput device that can passively separate motile sperm from the rest of the semen sample was created. The passive nature of the microfluidic system promises to conserve the viability and quality of the sperm for applications such as in vitro fertilization. This device can separate sperm with velocities higher than a cut off, which is tunable with the injection rate. The unprecedented efficiency of the device of the present application in comparison with previous studies, and its benign passive nature, make it favorable for sperm separation.

The design of the microfluidic system for sperm separation relied upon the generation of rheotaxis zones in front of a microfluidic corral system. The minimum shear rate within the rheotaxis zone for sperm to undergo rheotaxis was experimentally measured. Additionally, by experimentally extracting the sperm movement distribution within the rheotaxis zone, the role of rheotaxis in increasing the number of corralled sperm was demonstrated. Moreover, by providing a model for sperm movement inside the rheotaxis zone, and comparing that with experimental data, it is possible quantify the motility-based selection of the device as a function of flow/shear rate.

The microfluidic device is simple to use and effective, corralling only sperm with progressive and normal motility capable of upstream swimming and ensuring that the number of dead sperm within the corral is zero, resulting in a separation efficiency of 100%. It was also demonstrated that sperm separation by the microfluidic system of the present application is dependent on flow rate. By using different fluid injection rates (e.g., 0.6, 1.2, and 1.8 mL/h), the device is capable of selecting sperm with motilities higher than a tunable minimum cutoff. Additionally, demonstrated was how retainers fabricated inside the corral system increased the residence time of the sperm within the corral from ~12 s to 45 min.

These findings can have a broad range of applications, including the dairy and beef industry. As demonstrated, the microfluidic system of the present application can be used to separate motile bovine sperm as well. The device could further be used for clinical studies on human sperm and for ARTs. Improved sperm sorting could also be beneficial for fundamental studies on the physical, biological, and physiological attributes of sperm. Rheotactic behavior is not only observed in sperm, but is a general phenomenon observed in other microswimmers, such as bacteria. Even though rheotaxis varies among species and can be both positive or negative, rheotaxis-based separation using microfluidic systems could be investigated for other types of microswimmers.

Although preferred embodiments have been depicted and described in detail herein, it will be apparent to those skilled in the relevant art that various modifications, additions, substitutions, and the like can be made without departing from the spirit of the present application and these are therefore considered to be within the scope of the present application as defined in the claims which follow.

What is claimed:

1. A microfluidic system for separation of motile sperm from immotile sperm or motile bacteria from immotile bacteria, said system comprising:
   a housing having a first end and a second end and containing a passage connecting the first and second ends;
   an inlet at the first end of said housing for charging fluids into the passage proximate to the first end of said housing;
   an outlet at the second end of said housing for discharging fluids from the passage proximate to the second end of said housing, whereby fluid flows from said inlet, through the passage, and into said outlet; and
   one or more corrals within the passage, each of said corrals comprising a closed side and a partially open side, wherein the closed side is closer to the first end than the partially open side with the closed side and partially open side defining between them a confinement region suitable for retaining motile sperm or motile bacteria, and wherein the one or more corrals further comprise a wall member located opposite the closed side of the one or more corrals to define a pair of openings at opposite ends of the wall member leading to the confinement region.

2. The system of claim 1, wherein the system comprises a plurality of corrals spaced apart within the passage.

3. The system of claim 1, wherein the one or more corrals have a convex polygonal configuration.

4. The system of claim 1, wherein the one or more corrals have a configuration selected from the group consisting of a C-shaped configuration, a triangular-shaped configuration, a rectangular configuration, a pentagonal configuration, an oval configuration, a square configuration, and a semicircular configuration.

5. The system of claim 1, wherein the one or more corrals comprise one or more retainers to maintain motile sperm or bacteria within the confinement region.

6. The system of claim 1, wherein the one or more corrals are configured and arranged within the passage to form a rheotactic region proximate to the partially open side of each of the one or more corrals.

7. The system of claim 1, wherein the corrals per system range from 1 to about 100 in number.

8. The system of claim 7, wherein there are a plurality of corrals spaced apart by a distance ranging from about 100 µm to about 1000 µm.

9. The system of claim 1, wherein each corral has a maximum exterior dimension of about 80 µm to about 1 mm.

10. The system of claim 1, wherein the confinement region has a maximum interior dimension from about 5 µm to about 2 mm.

11. The system of claim 1, wherein there are one or more gaps between the closed side and the partially open side with each gap ranging from about 10 µm to about 500 µm.

12. The system of claim 1 further comprising:
   a pump positioned to move fluids within the passage from the first end of the housing to the second end of the housing.

13. A method for separation of motile sperm from immotile sperm or motile bacteria from immotile bacteria, said method comprising:
   providing the system of claim 1;
   providing a sperm-containing sample or a bacteria-containing sample; and
   passing the sperm-containing sample or the bacteria-containing sample through the inlet, through the passage, and through the outlet of said system, whereby motile sperm or motile bacteria are retained within the one or more corrals, while immotile sperm or immotile bacteria are discharged through the outlet.

14. The method of claim 13, wherein the sample comprises sperm.

15. The method of claim 13, wherein the sample comprises bacteria.

16. The method of claim 13 further comprising:
   recovering motile sperm or motile bacteria from the one or more corrals.

17. The method of claim 16, further comprising:
   washing the sample prior to said recovering the motile sperm or motile bacteria.

18. The method of claim 16, wherein motile sperm are recovered.

19. The method of claim 16, wherein motile bacterial are recovered.

20. The method of claim 18 further comprising:
   utilizing the recovered motile sperm in conjunction with an assisted reproductive technology.

21. The method of claim 13 further comprising:
   controlling flow of the sample through the housing to selectively retain the sperm or the bacteria within the one or more corrals.

22. The method of claim 21, wherein the flow of sample through the housing is at a rate ranging from about 0.5 mL/hr to 500 mL/hr.

* * * * *